US012029889B2

(12) United States Patent
Karas et al.

(10) Patent No.: US 12,029,889 B2
(45) Date of Patent: Jul. 9, 2024

(54) PERFUSION SYSTEMS AND METHODS FOR MONITORING TISSUE OXYGENATION AND REDUCING LIMB ISCHEMIA

(71) Applicant: Tulyp Medical SAS, Paris (FR)

(72) Inventors: Richard H. Karas, Franklin, MA (US); Tim Lenihan, Hradec Kralove (CZ); John McCarthy, Newbury, NH (US)

(73) Assignee: Tulyp Medical SAS, Paris (FR)

( * ) Notice: Subject to any disclaimer, the term of this patent is extended or adjusted under 35 U.S.C. 154(b) by 0 days.

(21) Appl. No.: 18/193,513

(22) Filed: Mar. 30, 2023

(65) Prior Publication Data
US 2023/0310833 A1    Oct. 5, 2023

Related U.S. Application Data

(60) Provisional application No. 63/362,363, filed on Apr. 1, 2022.

(51) Int. Cl.
*A61M 60/34* (2021.01)
*A61M 60/109* (2021.01)
(Continued)

(52) U.S. Cl.
CPC .......... *A61M 60/34* (2021.01); *A61M 60/109* (2021.01); *A61M 60/295* (2021.01); *A61M 60/38* (2021.01); *A61M 60/585* (2021.01); *A61M 60/843* (2021.01); *A61M 2205/3331* (2013.01)

(58) Field of Classification Search
CPC .. A61M 60/34; A61M 60/109; A61M 60/295; A61M 60/38; A61M 60/585; A61M 60/843; A61M 2205/3331; A61M 2205/3344; A61M 2205/50; A61M 1/1698; A61M 1/3609; A61M 1/3639; A61M 1/3659; A61M 1/3613; A61B 5/026; A61B 5/4848; A61B 5/02152
See application file for complete search history.

(56) References Cited

U.S. PATENT DOCUMENTS 3,877,843 A    4/1975  Fischel
3,963,023 A    6/1976  Hankinson
(Continued)

FOREIGN PATENT DOCUMENTS

WO    WO-2020161586 A1    8/2020

OTHER PUBLICATIONS

Artio Medical, Amplifi™, Vein Dilation System, https://artio.com/product/amplifi/, accessed Mar. 28, 2023.
(Continued)

*Primary Examiner* — Eugene T Wu
(74) *Attorney, Agent, or Firm* — Greenberg Traurig, LLP; Christopher C. Bolten

(57) ABSTRACT

Perfusion systems and methods are provided for increasing peripheral blood flow to reduce limb ischemia, in which an extracorporeal pump having a controller, and catheter/tubing set, employed alone or in conjunction with an interventional or circulatory assist device, withdraws blood from a patient's vasculature and reintroduces that blood at another location within the patient's vasculature at a controlled local pressure or flow rate, without interfering with operation of the interventional or circulatory assist device or surgical intervention.

28 Claims, 12 Drawing Sheets

(51) Int. Cl.
  *A61M 60/295* (2021.01)
  *A61M 60/38* (2021.01)
  *A61M 60/585* (2021.01)
  *A61M 60/843* (2021.01)

(56) References Cited

U.S. PATENT DOCUMENTS

| | | | |
|---|---|---|---|
| 4,080,958 | A | 3/1978 | Bregman et al. |
| 4,221,548 | A | 9/1980 | Child |
| 4,231,354 | A | 11/1980 | Kurtz et al. |
| 4,468,177 | A | 8/1984 | Strimling |
| 4,540,399 | A | 9/1985 | Litzie et al. |
| 4,666,425 | A | 5/1987 | Fleming |
| 4,998,914 | A | 3/1991 | Wiest et al. |
| 5,069,661 | A | 12/1991 | Trudell |
| 5,330,433 | A | 7/1994 | Fonger et al. |
| 5,338,662 | A | 8/1994 | Sadri |
| 5,423,745 | A * | 6/1995 | Todd ................. A61M 25/1034 604/509 |
| 6,458,323 | B1 | 10/2002 | Boekstegers |
| 6,508,777 | B1 | 1/2003 | Macoviak et al. |
| 6,555,057 | B1 | 4/2003 | Barbut et al. |
| 6,699,231 | B1 | 3/2004 | Sterman et al. |
| 6,808,508 | B1 | 10/2004 | Zafirelis et al. |
| 7,150,711 | B2 | 12/2006 | Nüsser et al. |
| 7,614,997 | B2 | 11/2009 | Bolling |
| 7,766,853 | B2 | 8/2010 | Lane |
| 7,819,835 | B2 | 10/2010 | Landy et al. |
| 8,267,881 | B2 | 9/2012 | O'Mahony et al. |
| 8,795,253 | B2 | 8/2014 | Moshinsky et al. |
| 8,834,404 | B2 | 9/2014 | Beaudin |
| 9,155,827 | B2 | 10/2015 | Franano |
| 9,211,372 | B2 | 12/2015 | Kaye |
| 9,295,767 | B2 | 3/2016 | Schmid et al. |
| 9,555,174 | B2 | 1/2017 | Franano et al. |
| 9,662,431 | B2 | 5/2017 | Franano et al. |
| 9,782,279 | B2 | 10/2017 | Kassab |
| 10,258,730 | B2 | 4/2019 | Franano et al. |
| 10,265,460 | B2 | 4/2019 | Gilbert |
| 10,426,878 | B2 | 10/2019 | Franano |
| 10,537,674 | B2 | 1/2020 | Franano |
| 10,780,250 | B1 | 9/2020 | Arepally et al. |
| 11,033,672 | B2 | 6/2021 | Turner |
| 11,471,596 | B2 | 10/2022 | Pile-Spellman et al. |
| 2006/0015065 | A1 * | 1/2006 | Kumazaki ........... A61M 1/3613 604/101.04 |
| 2006/0270895 | A1 | 11/2006 | Viole et al. |
| 2016/0331899 | A1 | 11/2016 | Laghi |
| 2019/0282741 | A1 | 9/2019 | Franano et al. |
| 2020/0023111 | A1 | 1/2020 | Franano |
| 2020/0155752 | A1 | 5/2020 | Franano |
| 2020/0246531 | A1 * | 8/2020 | Lenihan ............. A61M 1/3659 |
| 2021/0052280 | A1 | 2/2021 | Pillai |

OTHER PUBLICATIONS

Gaughan, et al., efemoral: Microaxial perfusion Pump to Mitigate Critical Limb Ischemia, Department of Biomedical Engineering—Carnegie Mellon University, Pittsburg, PA, https://www.cmu.edu/bme/Academmics/undergraduate-programs/Resources/design/2020-design-projects/4-wholeybloodassistpump.pdf, accessed Mar. 28, 2023.

Hakkel, Integrated near-infrared spectral sensing, Nature Communications, 13(1):103 (Jan. 2022).

Holland, et al., Lower Extremity Volumetric Arterial Blood Flow in Normal Subjects, Ultrasound in Med. & Biol., 24(8):1079-1086 (Oct. 1998).

Pahuja, et al., Incidence and Clinical-Outcomes of Bleeding Complications and Acute Limb Ischemia in STEMI and Cardiogenic Shock, Catheter Cardiovasc. Interv., 97(6):1129-1138 (May 2021).

International Search Report & Written Opinion dated Aug. 29, 2023 in Int'l PCT Patent Appl. Serial No. PCT/US2023/065170 (0110).

Lane, et al., Hypertensive extracorporeal limb perfusion (HELP): A new technique for managing critical lower limb ischemica, Journal of Vascular Surgery, 48(5):1156-1165 (2008).

* cited by examiner

PERFUSION SYSTEMS AND METHODS FOR MONITORING TISSUE OXYGENATION AND REDUCING LIMB ISCHEMIA

CROSS-REFERENCE TO RELATED APPLICATIONS

The disclosure claims priority to and the benefit of U.S. Provisional Patent Application No. 63/362,363, filed Apr. 1, 2022, which is hereby incorporated by reference herein in its entirety.

FIELD OF THE INVENTION

The present invention relates generally to systems and methods for monitoring tissue oxygenation and reducing ischemia by providing enhanced perfusion to a patient's extremities. In particular, the inventive system and methods may be employed for the treatment of any condition that induces limb ischemia including thrombotic or thromboembolic vascular occlusion or during medical procedures that involve use of devices that impede vascular blood flow (e.g., heart or vascular surgery, coronary or cardiac catheterization, insertion of cardiac support devices and/or following treatment to address peripheral artery disease and/or surgeries or interventions requiring tourniquets) or other causes of acute limb ischemia, in patients with shock or trauma, or in patients with existing peripheral arterial disease.

BACKGROUND

Decreased blood flow to and/or pressure within a patient's extremities, e.g., legs and arms, may arise from any of a number of causes, resulting in an acute or chronic ischemia of the limbs. During an interventional procedure, such as a percutaneous cardiac intervention, such as stenting, cardiac valve repair, or coronary or cardiac catheterization, a catheter may be placed in a patient's vasculature that obstructs flow in that vessel. Similarly, placement of a circulatory support device in a vessel, such as a percutaneous ventricular assist device (pVAD), intra-aortic balloon pump (IABP), or cannula for an extracorporeal membrane oxygenator system (ECMO) may occlude downstream flow in the vicinity of the entry point of the circulatory support device.

Decreased flow to the extremities also may arise due to cardiogenic shock, for example, caused by myocardial infarction, myocarditis, pulmonary embolism, venous occlusion, rupture of a heart valve or heart muscle, and many other disease states, many of which manifest as an inability of the patient's heart to pump sufficient oxygenated blood to body organs. Reduced circulation due to cardiogenic shock may lead to chronic ischemia of the patient's extremities, which in turn may require amputation. Reduced peripheral circulation also may result from existing peripheral artery disease, and as side effect of a peripheral vascular intervention.

In addition, limb ischemia may also occur with use of medical tourniquets, which are commonly used in conditions of vascular trauma or during operations such as knee surgery to reduce bleeding in the operative field. Tourniquets will reduce both arterial and venous blood flow and if used for a prolonged period of time may induce limb ischemia. In these cases, the invention may enable arterial and venous blood flow using two bypass circuits for each respectively, thereby preserving limb perfusion with tourniquet(s) in place.

One approach for increasing blood flow to the extremities in patients suffering from poor peripheral circulation due to obstruction caused by placement of an interventional device (e.g., catheter shaft or cannula) or circulatory assist device (pVAD or IABP) in an iliac, femoral or axillary artery is to use tubing to create an extracorporeal shunt from a location upstream of the obstruction to a cannula inserted at a remote location, downstream of the obstructions, in the patient's arterial system. U.S. Pat. No. 9,782,279 to Kassab is one example of such a passive perfusion system. It has been observed, however, that such proposed solutions are ineffective in reducing limb ischemia, require ad hoc set up, and are associated with very high incidence of adverse outcomes, including prolonged hospital stay, limb amputation and increased mortality.

Further, quite apart from limb ischemia, medical complications may arise due to rapid and catastrophic blood accumulation in the pericardium that impede heart function, thereby reducing systemic circulation. One approach to reduce blood accumulation in the pericardium is to manually and repeatedly aspirate blood from the pericardium. This is done until the patient can be transported to an operating room, which can take between one and four hours.

In view of the foregoing, it would be desirable to provide systems and methods for monitoring tissue oxygenation and/or increasing blood pressure and flow to the extremities of a patient undergoing an interventional procedure or on a circulatory assist device, wherein an interventional device, circulatory assist device, tourniquet or other natural cause (i.e., thrombosis) creates an obstruction in any artery or vein (i.e., iliac, femoral, axillary, brachial artery or vein) and that overcomes the drawbacks of previously known solutions. In particular, it would be desirable to provide apparatus and methods for enhancing blood flow and maintaining blood pressure in the peripheral vasculature sufficiently to save the limb.

It further would be desirable to provide apparatus and methods for enhancing peripheral blood flow that reduce blood stagnation, particularly adjacent to a catheter or cannula insertion site, thereby reducing the risk of thrombus formation.

It still further would be desirable to provide apparatus and methods for increasing peripheral blood flow in patients undergoing vascular interventions or other surgical procedures including the use of tourniquets, and patients recovering from peripheral vascular interventions, that are designed to reduce a risk of blood leakage at a device insertion site.

SUMMARY OF THE INVENTION

The present invention is directed to systems and methods for monitoring tissue oxygenation, vascular or local pressure, and/or increasing peripheral blood flow and vascular pressure to reduce limb ischemia in patients with arterial or venous obstruction due to disease conditions or due to cardiac or vascular interventions, where the interventional device or tourniquet causes at least a partial obstruction of downstream blood flow. In accordance with the principles of the present invention, the inventive devices comprise an extracorporeal pump and cannula/tubing set that may be used alone or in conjunction with any procedure or device that obstructs blood flow, to withdraw oxygenated blood from a patient's vasculature or anatomic compartment (i.e., pericardium) and to reintroduce that blood at another location within the patient's vasculature at an independently controlled vasculature pressure or flow rate. In this manner, the blood flow rate or blood pressure may be independently controlled in the patient's extremities, without interfering with placement or operation of an interventional device or circulatory assist device. In a preferred embodiment, the flow rate may be adjusted in order to achieve a target vessel pressure to increase oxygenation of the tissue in the limb(s) experiencing, or at risk of experiencing, ischemia. Output from a near-infrared spectroscopy (NIRS) sensor, or other oxygen-sensing device applied to the affected limb may also be utilized as an input into the present inventive device to regulate the perfusion flow or pressure. Inlet suction pressure may also be used as a determinant of bypass flow.

In one preferred embodiment, the inventive system includes an inlet cannula configured to be placed in a patient's artery or vein, which includes a central lumen through which an interventional vascular device or circulatory assist device may be inserted. The inlet cannula may include a hemostatic valve and a side port through which blood passes from through the inlet cannula to an inlet of an extracorporeal pump. The extracorporeal pump then propels blood back into the patient's vasculature at a selected pressure or flow rate via a return lumen having an outlet downstream of the inlet cannula. In one embodiment, the outlet of the return lumen is embodied in a separate return cannula. In this embodiment, the return catheter may have a pressure sensor disposed near its outlet end for measuring pressure in the vessel, and the pump output may be automatically adjusted to maintain a desired pressure in the vessel. In addition, output from a NIRS sensor or other oxygen-sensing device for monitoring tissue oxygenation may additionally be used to provide input to a feedback loop that controls pump performance.

In an alternative embodiment, the inlet cannula and return lumen may be embodied in a single cannula. In one such embodiment, the return lumen is a second lumen of the inlet cannula and opens to a skive in a lateral surface of the inlet cannula, such that blood exiting the extracorporeal pump is returned to the vasculature downstream of an inlet of the inlet cannula. An occlusion balloon may be disposed near a distal end of the inlet cannula to partially or completely occlude antegrade blood flow through the artery, such that blood instead is directed to the extracorporeal pump and blood returned from the pump does not flow in a retrograde direction. In this manner, blood returned to the patient from the extracorporeal pump is delivered below the occlusion balloon in an antegrade direction to perfuse the patient's peripheral vasculature. The extracorporeal pump and/or cannula may include pressure and flow sensors for monitoring the inlet and outlet pressures and blood flow rates, and the extracorporeal pump may include a controller for determining and maintaining a physician-specified or automatically determined blood flow rate or pressure in the perfused vessel. The inlet cannula also may include a balloon, separate from the occlusion balloon, for sealing the cannula insertion site to prevent leakage.

In accordance with another aspect of the invention, the occlusion balloon may be configured to have a concave profile on its proximal face to direct flow exiting from the skive of the return lumen in an antegrade direction. Alternatively, or in addition, the distal face of the occlusion balloon may have a funnel shape, when inflated, to reduce the creation of stagnant blood zones. As a yet further alternative, the occlusion balloon itself may be perforated, so that blood directed into the balloon both expands the balloon into contact with the vessel wall, providing partial or complete occlusion, and then passes through the perforations to provide antegrade flow to the patient's extremities.

In still another embodiment, perfusion system may include an inlet catheter that is inserted into an iliac, femoral or axillary artery or vein and a smaller diameter return catheter that is inserted through the lumen of the inlet catheter. An extracorporeal pump is configured to suck blood through an annulus formed between the interior of the inlet catheter and the exterior of the return catheter. The blood is delivered by the extracorporeal pump through the return catheter and back into the vasculature at a downstream location closer to the extremity at a controlled pressure or flow rate. In a still further embodiment, the perfusion system may include multiple inlet cannulas to draw blood from both the arterial and venous vasculature, and multiple return catheters to provide enhanced perfusion to multiple limbs. In addition, multiple pumps or pump heads may be used that are independently controlled based on oxygenation, pressure or flow input from a given region of required perfusion.

Extracorporeal pumps suitable for use in the perfusion system of the invention may comprise any suitable commercially available blood pump design, including vane pumps, centrifugal pumps, diaphragm pumps, piston pumps and roller pumps. In one embodiment, the extracorporeal pump may be capable of generating pulsatile flow. In another embodiment, the extracorporeal pump may be capable of generating a non-pulsatile flow.

Other features of the inventive system and methods will be apparent with reference to the following description and figures.

DETAILED DESCRIPTION OF THE INVENTION

Figure 1:
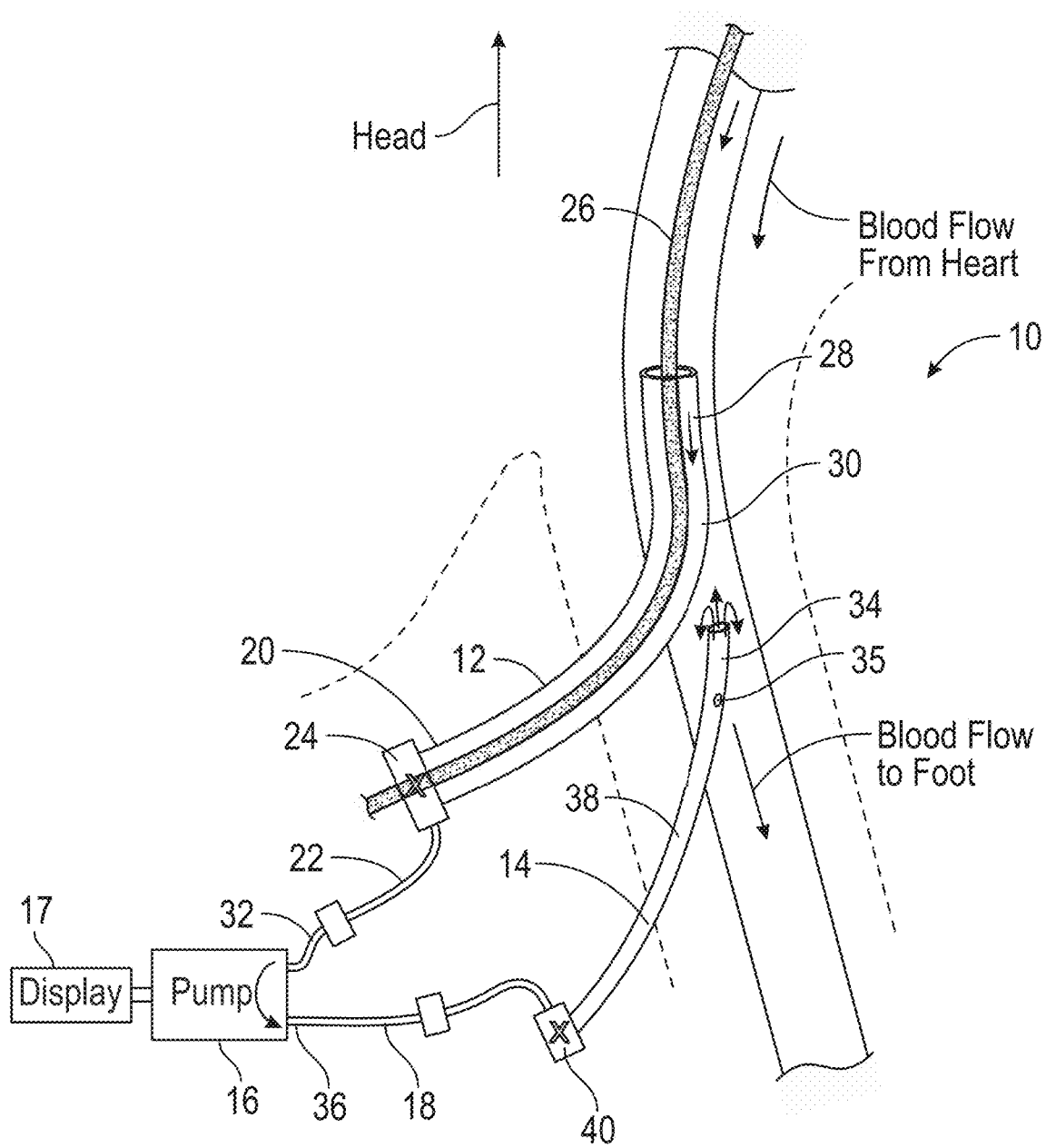
FIG. 1 is a schematic of a perfusion system constructed in accordance with the principles of the present invention, in which an extracorporeal pump is connected between an inlet catheter, through which interventional or circulatory assist device may be placed, and a return catheter.

The present invention is directed to a perfusion system for monitoring tissue oxygenation and/or enhancing perfusion to the extremities of a patient suffering from reduced blood flow to the extremities from any of a number of causes. Causes of such reduced blood flow may include placement of a percutaneous interventional device or circulatory assist device in an artery or vein that results in partial or complete occlusion of downstream blood flow in that vessel, or as an after effect of cardiogenic shock or peripheral artery disease, or as a results of any procedure requiring cessation of blood flow using tourniquets or other methods to stop blood flow to an area. In accordance with the principles of the invention, the perfusion system draws arterial blood from a location upstream of the obstruction or reduced-flow region, and delivers the blood back into the vessel, or an adjacent or contralateral vessel, with a controlled vasculature pressure or flow rate volume, thereby reducing a risk of limb ischemia. Further, the flow to the limb through the pump may be regulated by physiologic feedback such as tissue oxygen levels.

It is hypothesized that acute and/or chronic limb ischemia that occurs in patients during vascular intervention is due to partial or complete obstruction of downstream arterial or venous flow created by the presence of a blood clot, traumatic injury, tourniquet, or a catheter of an interventional device, or circulatory assist device. Other potential causes may include compromised cardiac output, arteriosclerosis, and/or generalized increased vascular hydraulic resistance in the limbs, all which may contribute to less flow in the extremities at lower localized pressure. Reduced peripheral flow and/or blood pressure in turn may contribute to increased thrombus formation, worsening limb ischemia, and increased risk of myocardial infarction, pulmonary embolism and stroke. Accordingly, to address these issues, the systems and methods of the present invention are designed to direct a portion of the blood flowing towards the extremities to an extracorporeal blood pump, which returns the flow to the same or another vessel at a controlled pressure or flow rate sufficient to reduce ischemia.

Other patients experience complications of interventional procedures such as coronary perforation, cardiac rupture, right heart free wall puncture due to biopsies, or rupture of the aorta or other valves during valve replacement may develop rapid and catastrophic blood accumulation in the pericardium, thereby impeding function of the native heart. As excess blood is removed from the pericardium, the patient may require a transfusion to replace the aspirated blood. The systems and methods of the present invention further are designed to direct a portion of accumulated blood to an extracorporeal blood pump, which returns the blood to systemic circulation.

As mentioned in the Background, some surgeons and interventional clinicians have sought to augment flow to a patient's extremities by using a tubing set to passively transfer blood from a higher pressure/flow region, e.g., an artery close to the heart, to a remote arterial location, e.g., in a femoral artery. Due to a number of factors, such attempts have not proven satisfactory due to the slow flow rates and low pressure inherent in such a passive system, as well as hydraulic resistance encountered in the tubing sets. Applicants hypothesize that even in the presence of substantial blood flow, the existence of low vasculature pressure in the limbs may drive insufficient oxygen absorption in the capillaries. It is the applicants' insight that by providing an extracorporeal blood pump, blood flow rates and vasculature pressures supplied to the patient's extremities may be better controlled to perfuse the extremities and reduce the risk of ischemia. In addition, provision of one or more separate extracorporeal pumps allows perfusion of the limbs to be controlled independently of operation of any vascular device or circulatory assist device that may create an obstruction. The systems and methods of the present invention further enable the clinician to monitor perfusion in the patient's extremities, and to adjust the flow to achieve a targeted pressure in the perfused vessel in real time. It should be known that when describing various embodiments, the terms "vessel pressure," "vascular pressure," "local pressure," "blood pressure," or some combination of these terms refers to the fluidic pressure within a patient's blood vessels and/or capillaries.

Referring now to FIG. 1, exemplary perfusion system 10 arranged in accordance with the principles of the present invention is described. System 10 includes inlet cannula 12, return cannula 14, and extracorporeal pump 16 coupled by tubing 18. Inlet cannula 12 is configured for placement in a femoral, iliac or axillary artery or vein and includes proximal end 20 having outlet port 22 and hemostatic port 24 through which an interventional device or circulatory assist device may be inserted to perform an interventional procedure or to assist cardiac function. Distal end 28 of inlet cannula 12 is configured to be placed in an antegrade direction in the vessel to assist in positioning of the interventional or circulatory assist device. Inlet cannula 12 has a sufficiently large diameter, e.g., 16-22 Fr, that annulus 30 is formed by the exterior surface of the device inserted there-through and the interior surface of inlet cannula 12, such that blood flow will pass to outlet port 22 and to inlet 32 of pump 16.

In an alternative or additional option, the inlet cannula may be a pigtail catheter that is inserted into the pericardium in the event of blood accumulation in the pericardium. The accumulated blood is then drained from the pericardium and auto-transfused into a vascular sheath through the return lumen. Such an embodiment would enable two life-saving treatments: 1) to drain the pericardium so blood does not build up and impede function of the heart; and 2) auto-transfuse patients so they do not require excess blood products.

In one embodiment, return cannula 14 may be configured to be placed in the patient's iliac, femoral or axillary artery or vein with outlet end 34 facing in a retrograde direction. In this orientation, blood delivered from outlet 36 of pump 16 through lumen 38 of return cannula 14 is directed against inlet cannula 12 to cause wash out of any stagnation zones created where inlet cannula 12 enters the vessel. Return cannula 14 also may include valve 40 at its proximal end. At least a portion of blood exiting outlet end 34 of return cannula 14 thus flows in a retrograde direction before flowing in an antegrade direction to the patient's extremities. Return cannula 14 also may have an infusion port to allow the pump circuit to be used simultaneously for blood transfusions and/or one or more delivery ports for the delivery of reperfusion protection agents or therapeutic agents to reduce or eliminate reperfusion injury. Such reperfusion protection or therapeutic agents may include, but are not limited to, anticoagulants and thrombolytics.

In alternative embodiments, the return cannula may be configured to be placed at a more distal location in the peripheral circulation, spaced apart from the insertion site of the occlusive sheath. For example, the return cannula may be placed in a vein or artery near the ankle when treating ischemia in a leg or placed in a vein or artery near the wrist when treating ischemia in an arm even though the ankle or wrist are not near the occlusion.

Extracorporeal pump 16 having display panel 17 may be a conventional, commercially available blood pump capable of either continuous or pulsatile flow that uses any number of known pumping technologies, such as a vane pump, diaphragm pump, gear pump, roller pump, centrifugal pump, axial flow pump, balloon-mounted pump or piston pump. In a preferred embodiment, extracorporeal pump 16 is driven by an electric motor, and includes a controller that permits the vessel pressure or flow rate to be adjusted. Display panel 17 may be a touchscreen device that enables operation of the pump to be adjusted, as well as to display the output of sensors disposed on the cannulas. In accordance with one aspect of the invention, extracorporeal pump 16 may include, or be in communication with, pressure sensors that sense blood pressure at the distal end 28 of inlet cannula 12 and outlet end 34 of return cannula 14, as well as measure flow rate through the pump, and sense the presence of obstructions. In such an embodiment where the pump controller is in communication with pressure sensors located within the vein or artery of the limb, it may be desirable to have the pressure sensors measure the local blood pressure through a lumen separate from any inlet or return lumen, such as a lumen described below in FIGS. 2 and 3. Use of a separate lumen may allow the local pressure to be transduced or measured independent of the flowing blood. One skilled in the art would understand that pressure sensors may also be located at inlet port 32 and outlet port 36. However, in such an embodiment with pressure sensors at the inlet and outlet ports, it may be desired to account for the drop in pressure caused by the friction in the pump circuit. Such a pressure drop may be accounted for by using a higher target pressure than the ideal target vessel pressure, reducing the friction in the pump circuit, or a combination of the two. For example, to reduce friction in the pump circuit, it may be desirable to coat the inner surface of the cannulas with a layer of polytetrafluoroethylene, such as Teflon™.

Further in accordance with the invention, the controller may include a processor programmed to sense vascular resistance at outlet port 36. The controller further may be programmed automatically to adjust the outlet pressure and flow rate to maximize limb perfusion while avoiding the use of excessive pressure, which might cause extravascular leakage and edema. In addition, extracorporeal pump 16 could be configured to generate a pulsatile flow at outlet 34 of return cannula 14 that mimics the pressure fluctuations of a normal cardiac cycle and thus reduces the risk of thrombus formation. As a further option, the pump may be synchronized with an ECG output or pressure wave sensor to eject blood during diastole, thereby reducing afterload on the heart. In a still further addition, the pump may be configured to oxygenate blood flowing through the pump in the event increasing vessel pressure or flow rate is insufficient. One skilled in the art would recognize the possibility of splicing a separate extracorporeal membrane oxygenator system (ECMO) to the pump circuit. In an alternative option, one inlet cannula may supply the pump with arterial blood while venous and/or transfusion blood may be fed through an ECMO before being fed into the pump. The pump then supplies the combination of this arterial blood and the oxygenated venous and/or transfused blood through the return lumen.

In accordance with another aspect of the invention, the extracorporeal pump may be configured to maintain perfusion pressure rather than a selected output flow. For example, the extracorporeal pump may deliver blood so that the mean perfusion pressure in the limb, e.g., leg or arm, is maintained by continually varying the flow rate. In addition, the supply of blood delivered to the pump may be from other parts of the body, e.g., arm or other leg, and not simply upstream of the vessel in which blood is reperfused. Further, the controller of the pump may be in communication with sensors that measure the oxygenation of the blood and/or tissue in the limb being reperfused. Such sensors may use various measurement standards such as, for example, measuring levels of blood-oxygen saturation ($SpO_2$), arterial blood gas ($PaO_2$), Near Infrared Spectroscopy (NIRS) to measure absolute tissue saturation ($StO_2$), pH levels, or lactate levels. For example, return cannula 14 may include integrated NIRS sensor 35 proximate to its distal end for measuring tissue oxygenation levels of the tissue surrounding the cannula at the reperfusion site. An example of an integrated NIRS sensor suitable for such use is described in the article by K. D. Hakkel et al., entitled "Integrated near-infrared spectral sensing," Nature Communications, 13:103 (2022), available at https://doi.org/10.1038/s41467-021-27662-1. In this case, the controller of the extracorporeal pump may provide on display 17 a readout of the flow rate, local blood pressure in the perfused vessel and level(s) of tissue oxygenation. The controller also may be programmed, e.g., via display panel 17, to permit an operator to select a combination of cycle length and outflow pressure that provides the highest flow at the target vessel pressure to achieve or maintain a target tissue oxygenation level.

Preferably, the controller of the extracorporeal pump has multiple operating modes. In each operating mode, the feedback loop controlling the pump is based on a different measured variable. In flow mode the operator will manually set the flow rate at which the pump will perfuse the extremity. In vascular or local pressure control mode, the system will perfuse the leg at a specific vascular pressure and this target pressure will be either manually or automatically determined. Similarly, in tissue oxygen control mode, the system will perfuse the extremity to achieve a specific tissue oxygen level and this target oxygen level will be either manually or automatically determined. In any of these modes, the measured variable may be either manually entered or automatically determined by the artificial intelligence component. The software of the controller also may include an artificial intelligence component that prompts the controller to reassess this selected combination at various intervals of time to optimize settings that work best for a particular patient. Alternatively, the pump circuit may serve as a passive bypass circuit until the controller senses a drop in tissue oxygenation levels that may result in limb ischemia via sensor 35. Once the controller senses a drop in the tissue oxygenation level below a predetermined value, the controller may automatically activate the pump.

In accordance with another aspect of the invention, the pump may have two or more return cannulas where each return cannula is supplying blood to a different limb, each return cannula is supplying blood to different areas or veins/arteries of the same limb, or each return cannula is supplying blood different areas of multiple limbs such as supplying blood to both an upper portion and a lower portion of a leg at the same time as supplying blood to an arm proximate to the shoulder and proximate to the wrist. In such an embodiment, it may be desirable to maintain either a constant flow rate or a constant vessel pressure for some or all limbs being reperfused. Otherwise, the use of pressure control or flow rate control valves may be desired to change the flow rate or pressure in one limb without changing the flow rate or pressure in another limb. The inlet cannula alternatively may be coupled to multiple pumps or a single pump having multiple stages, such that each pump or stage is employed to reperfuse a different limb. In such an embodiment, each limb may have their own, individual flow rates or vessel pressures maintained. As another alternative, there may be multiple inlet cannulas that each supply blood to the same or different pumps or motors. In such an embodiment, it may be desirable to have each inlet cannula inserted into a different vein or artery or a supply of transfusion blood. The blood reperfusion system may use any combination of the multiple return and inlet cannulas and single or multiple pumps or motors. These inlet cannulas may then either supply blood to the same pump, two different pumps, or one or both inlet cannulas may supply blood to more than one pump. When both inlet cannulas are supplying blood to the same pump, the pump may have one or more return cannulas. When the inlet cannulas are supplying blood to multiple pumps, each pump may have one or more return cannulas. When there is more than one return cannula, each return cannula may supply blood to different limbs, different areas of the same limb, different veins and/or arteries of the same limb, or some combination of the aforementioned.

Figure 13:
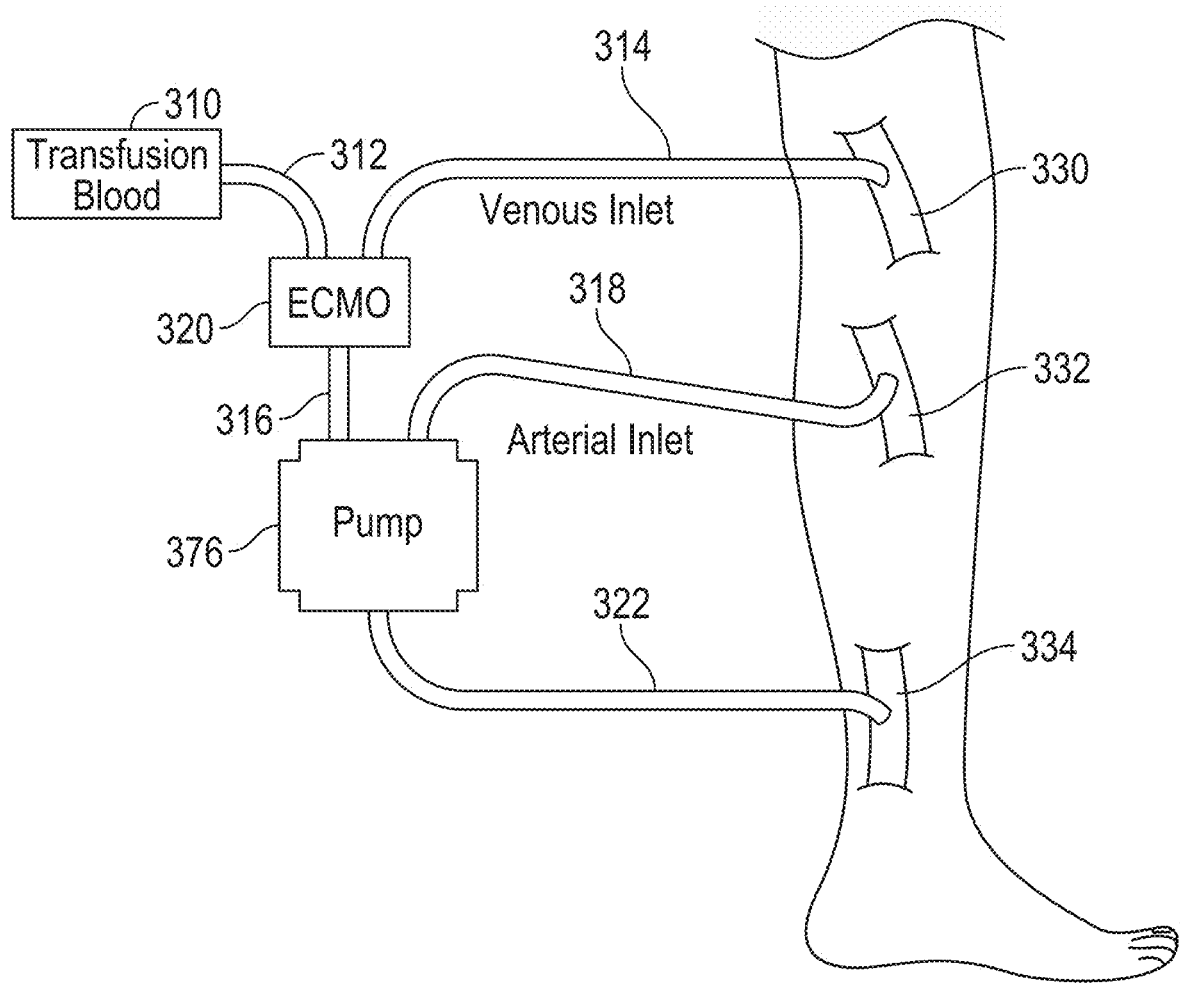
FIG. 13 is another alternative embodiment of the perfusion system of FIG. 1, in which the extracorporeal pump is fed by two inlet cannulas and returns blood through one return cannula.

For example, referring to FIG. 13, pump 376 may have two inlet cannulas and one return cannula. The first inlet cannula may be arterial inlet cannula 318 inserted into artery 332 of a limb while the second inlet cannula of pump 376 is oxygenated inlet cannula 316 that carries oxygenated blood from ECMO 320. ECMO 320 may be supplied by venous inlet cannula 314 and transfusion cannula 312 where the transfusion cannula supplies the ECMO with transfusion blood 310. The blood supplied to pump 376 by arterial inlet cannula 318 and oxygenated inlet cannula 316 is then mixed before being returned to vein or artery 334 through return cannula 322. One skilled in the art would understand that any number of other possible combinations exist. For example, the pump may have three inlets. One inlet for transfusion blood, one inlet for venous blood, and one inlet for arterial. In such an embodiment, the ECMO may be omitted or it may only oxygenate one of the transfusion blood, venous blood, or arterial blood. The pump also may have more than one return cannula where each return cannula returns blood to different areas of the limb or to different limbs. In such an embodiment, the pump may or may not mix the inlet blood before supplying it to the return cannulas. As a further option, the reperfusion system may have more than one pump or motor. For example, there may be a single pump or motor for each inlet and/or each return. In another example, there may be one pump or motor for venous inlet cannulas and one pump or motor for all arterial inlets cannulas.

In accordance with another aspect of the invention, the device may be used to provide flow to one or more vascular compartments. For example, using a single motor and single console or independent motors and consoles, two rotors can be used to bypass two arteries or an artery and a vein or two veins. This application is particularly useful when full occlusion of blood flow to and from an extremity has occurred or is required as in the case of a tourniquet. In this case, the device would provide antegrade arterial flow to the limb and retrograde venous flow from the leg. This will enable optimal limb perfusion. In another example, the multi-rotor device can provide arterial bypass to both legs or to a leg and an arm simultaneously.

Figure 2A:
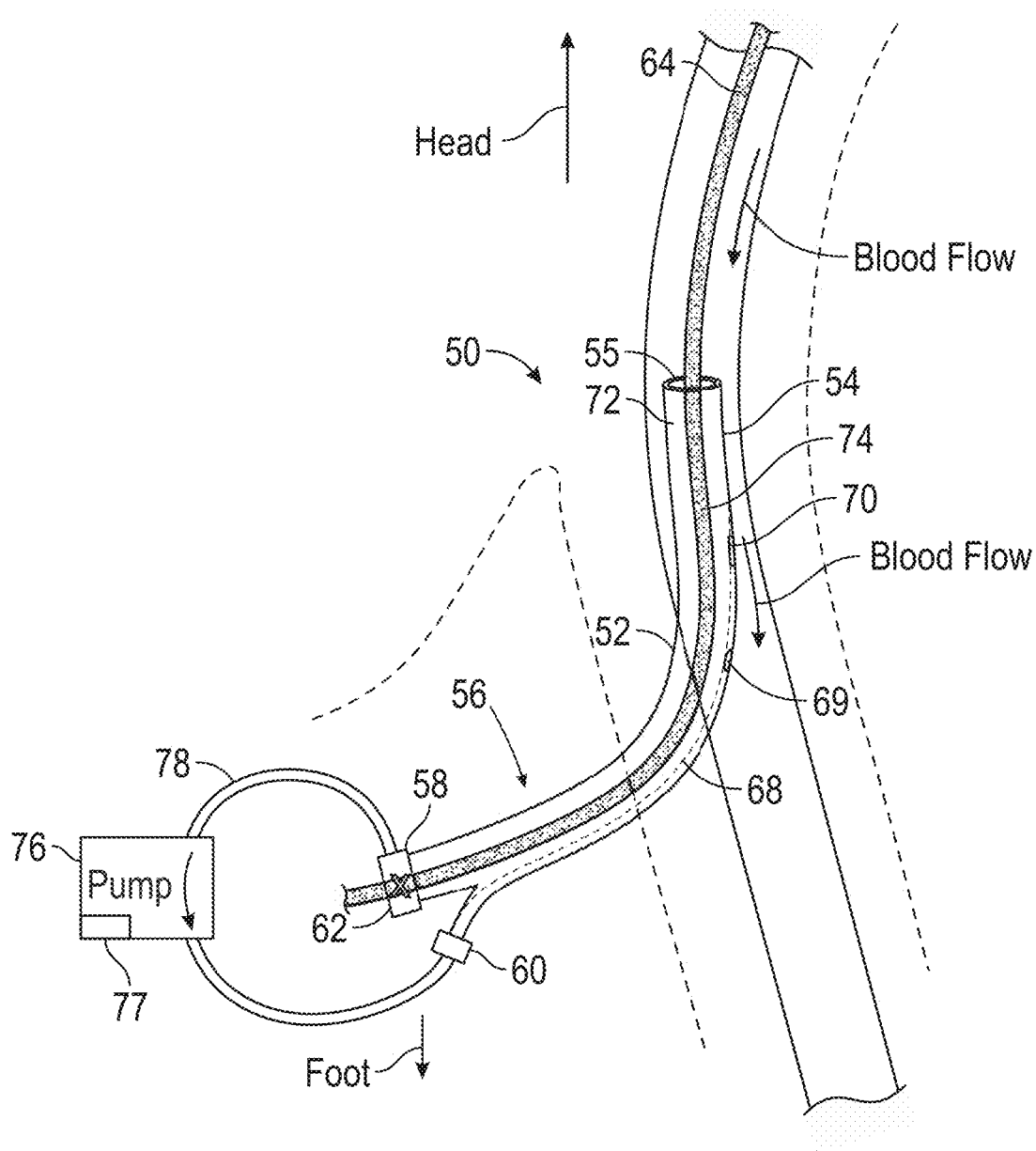
FIGS. 2A and 2B are, respectively, a schematic of an alternative embodiment of the perfusion system of the present invention in which features of the inlet and return catheters of the embodiment of FIG. 1 are integrated into a double lumen catheter, and a cross-section of the double lumen catheter.
Figure 2B:
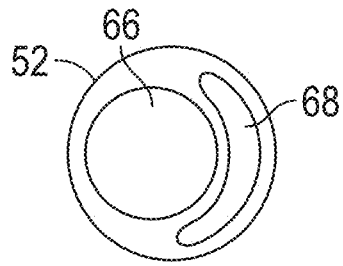

Turning now to FIGS. 2A and 2B, an alternative embodiment of a perfusion system constructed in accordance with the principles of the present invention is described. Perfusion system 50 is designed to provide similar functionality to system 10 of FIG. 1, but employs double lumen cannula 52 instead of separate inlet and return cannulas. Cannula 52 includes distal end 54 having inlet 55, proximal end 56 having valved inlet port 58 and outlet port 60, and hemostatic valve 62 through which interventional or circulatory assist device 64 may be inserted. As depicted in FIG. 2B, cannula 52 has inlet lumen 66 and outlet lumen 68, which opens to skive 70 at a location proximal of distal end 54. NIRS sensor 69 may be located downstream of skive 70 to sense tissue oxygenation in the reperfused region. Inlet lumen 66 is sufficiently large that annulus 72 forms around shaft 74 of device 64, so that extracorporeal pump 76 may draw blood from the vessel through inlet 55 of distal end 54, annulus 72 and inlet port 58. Extracorporeal pump 76 is coupled to inlet port 58 and outlet port 60 of cannula 52 via tubing 78, so that blood exiting pump 76 passes through outlet port 60, lumen 68 and skive 70. Pump 76 may include built-in display panel 77 that serves as both an input device and display screen.

Extracorporeal pump 76 may be configured as described for the embodiment of FIG. 1, and preferably includes pressure and flow sensors for monitoring flow characteristics, such as local blood pressure and flow rates, at the distal ends of the inlet and return cannulas. In addition, pump 76 may be configured to provide pulsatile flow to skive 70 to perfuse the extremities at controlled pressures or flow rates. It is expected that although skive 70 is opposed to the vessel wall, flow through lumen 68 will be sufficient to locally move cannula 52 away from the vessel wall to permit blood to freely flow in an antegrade direction.

Figure 3A:
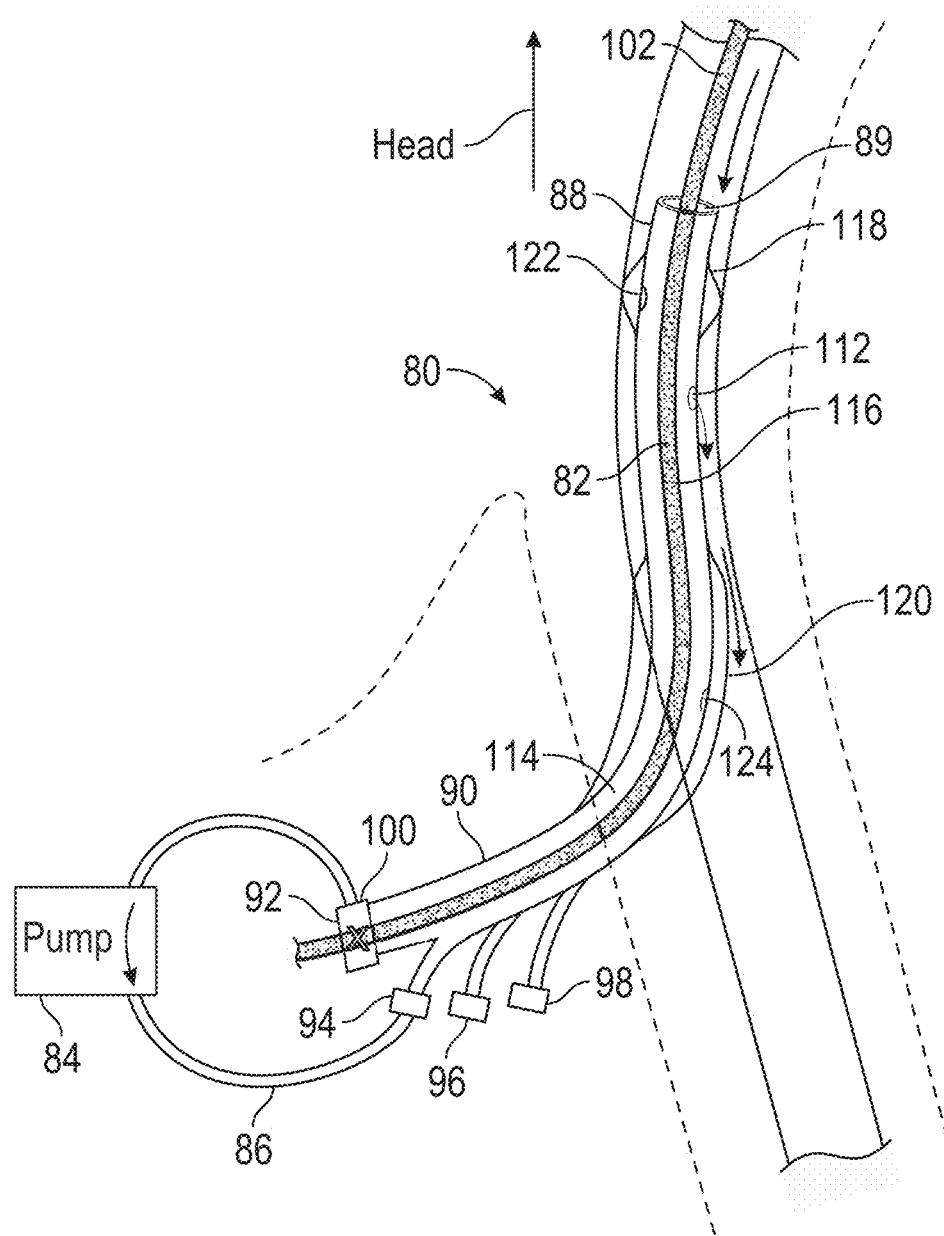
FIGS. 3A and 3B are, respectively, a further embodiment similar to the embodiment of FIGS. 2, but further including an occlusion balloon for partially or fully occluding antegrade flow through the vessel and a sealing balloon for preventing excessive blood loss through the opening through which the perfusion cannula is inserted into the vessel.
Figure 3B:
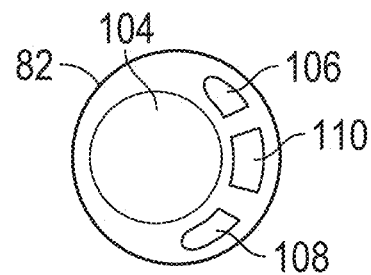

Referring now to FIGS. 3A and 3B, a further alternative embodiment of a perfusion system of the present invention is described. System 80 includes multi-lumen cannula 82 coupled to extracorporeal pump 84 via tubing 86. Extracorporeal pump 84 suitable for use with cannula 82 may have any of the features for the embodiments described for the perfusion systems of FIGS. 1 and 2. Cannula 82 is similar in design to cannula 52 of the embodiment of FIGS. 2A and 2B, except that it further includes an occlusion balloon and an optional sealing balloon.

More specifically, cannula 82 includes distal end 88 having inlet 89, proximal end 90 having valved inlet port 92 and outlet port 94, balloon inflation ports 96 and 98, and hemostatic valve 100 through which interventional or circulatory assist device 102 may be inserted. As shown in FIG. 3B, cannula 82 has inlet lumen 104, balloon inflation lumens 106 and 108, and outlet lumen 110, which opens to skive 112 at a location proximal of distal end 88. Inlet lumen 104 is sufficiently large that annulus 114 forms around shaft 116 of device 102, so that extracorporeal pump 84 may draw blood from the vessel through inlet 89 of distal end 88, annulus 114 and inlet lumen 110. Extracorporeal pump 84 is coupled to inlet port 92 and outlet port 94 of cannula 82 via tubing 86, so that blood exiting pump 84 passes through outlet port 94, lumen 110 and skive 112.

Still referring to FIGS. 3A and 3B, cannula 82 further includes occlusion balloon 118 disposed between distal end 88 and skive 112 to partially or completely block antegrade flow through the vessel, and optional elongated sealing balloon 120 disposed proximal of skive 112 to reduce blood leakage around cannula 82 where it enters the vessel. Occlusion balloon 118 is in fluid communication with inflation port 96 via inflation lumen 106, and aperture 122, which opens to the interior of occlusion balloon 118. Likewise, sealing balloon 120 is in fluid communication with inflation port 98 via inflation lumen 108 and aperture 124, which opens to the interior of sealing balloon 120. Occlusion balloon 118 preferably comprises a semi-compliant material, such as nylon, or compliant material such as polyurethane, which enables the balloon to conform to the diameter of the vessel to occlude, partially or fully, antegrade flow. Sealing balloon 120 preferably comprises a more rigid material, such as polyethylene terephthalate, which holds its shape during expansion, to provide tight approximation to the entry wound through which cannula 82 is inserted into the vessel. In particular, sealing balloon 120, if provided, may be inflated via inflation port 98 if, during operation of pump 84, the insertion site begins to bleed, thus stopping the bleeding and directing the blood exiting from skive 112 toward the patient's extremities.

Figure 4A:
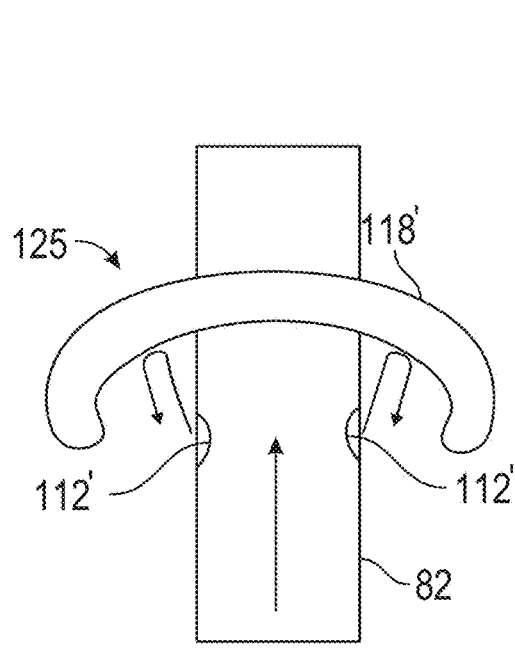
FIGS. 4A and 4B are, respectively, a side view of an embodiment in which the inlet catheter includes a concave occlusion balloon to direct reperfused blood, and a side view of another alternative embodiment in which a perforated material is disposed over the skive of the return lumen to more evenly distribute blood reperfused into an vessel.
Figure 4B:
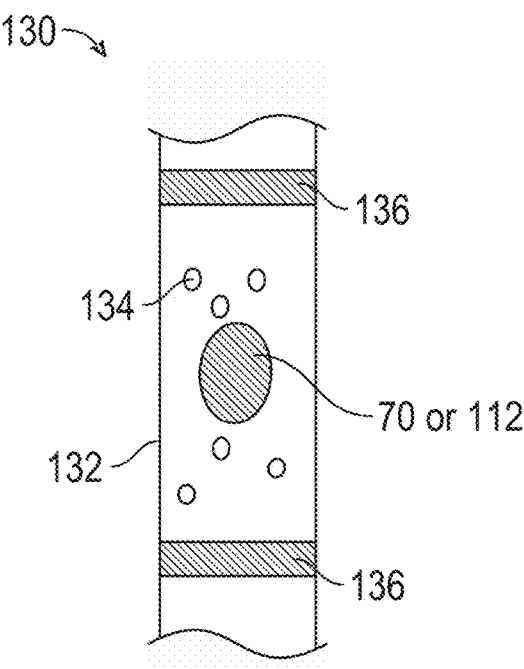

Referring to FIGS. 4A and 4B, alternative structures for more evenly distributing blood exiting from skive 70 of cannula 52 of FIG. 2 or skive 112 of cannula 82 of FIG. 3 is now described. In FIG. 4A, a portion of cannula 82 of FIG. 3 is depicted having multiple skives 112' and occlusion balloon 118' disposed distal to skives 112'. When inflated, occlusion balloon 118' assumes concave shape 125, such that blood exiting skives 112' impinges of the proximal surface of the balloon and is redirected in an antegrade direction. Occlusion balloon 118' may be molded to assume concave shape 125 during manufacture. In this manner, blood reperfused into the vessel from the extracorporeal pump may be more evenly redistributed and directed in an antegrade direction within the vessel without directly impinging upon the vessel wall.

FIG. 4B shows an alternative structure that may be used to distribute flow returned through skive 70 of cannula 52 or skive 112 of cannula 82. Diffuser 130 comprises a thin-walled layer of shrink tubing 132 that includes a multiplicity of holes 134, and is affixed to the cannula over the skive 70 of cannula 52, or skive 112 of cannula 82, to more evenly distribute blood returned from the extracorporeal pump. In particular, diffuser 130 may be bonded to the cannula using a heat weld or suitable biocompatible glue along lines 136. Diffuser 130 reduces the risk that blood returned to the vessel through the skive will jet against the vessel wall at high velocity. In addition, diffuser 130 may be readily flushed with saline prior to use without causing the cannula to become bulky or impede insertion. In such embodiments of FIGS. 3A and 3B, it may be desirable to place the local blood pressure sensor in the vessel downstream of diffuser 130.

Figure 5A:
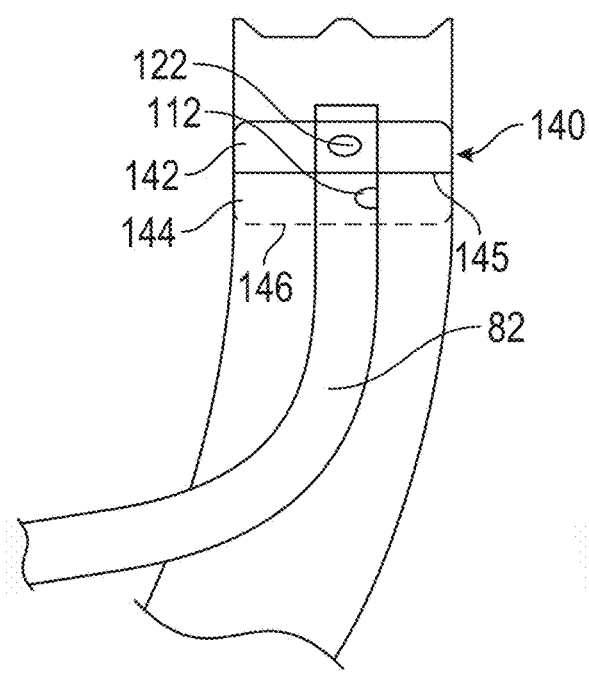
FIGS. 5A and 5B, are, respectively, an embodiment in which the occlusion balloon and skive of FIG. 3 are replaced by a balloon having a distal portion that occludes antegrade flow and a perforated proximal portion through blood is returned to the vessel; and an alternative embodiment wherein the distal and proximal faces of the balloon are inclined, relative to the axis of the cannula to form distal funnel and an enlarged proximal area for dispersing blood delivered by the extracorporeal pump.
Figure 5B:
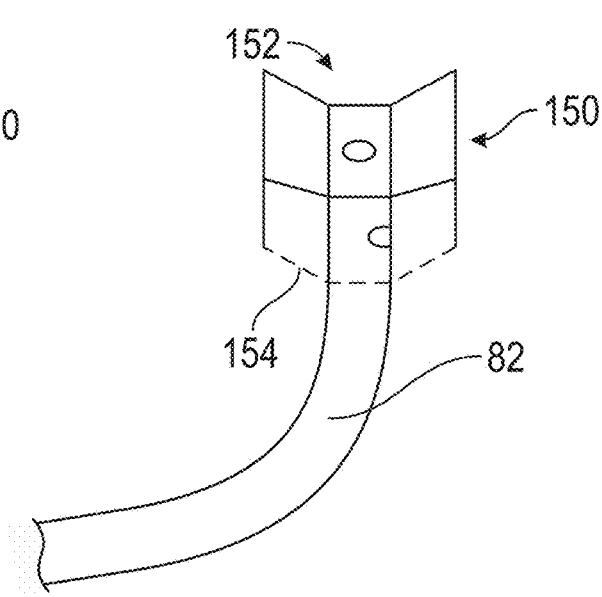

FIGS. 5A and 5B depict additional modifications that may be made to cannula 82 of the embodiment of FIGS. 3A and 3B. FIGS. 5A and 5B depict the distal end of the perfusion cannula (e.g., cannula 82), and omits the interventional or circulatory assist device, which may extend through the inlet lumen of the cannula and distal end. In the embodiment of FIG. 5A, occlusion balloon 118 and skive 112 are combined into dual layer balloon 140. Balloon 140 may be formed of a semi-compliant material, such as nylon, or compliant material such as polyurethane, and includes upper compartment 142 separated from lower compartment 144 by fluid impermeable membrane 145. Sealed upper compartment 142 is configured to expand into contact with the vessel wall when filled with saline through aperture 122. Lower compartment 144 is in fluid communication with skive 112, and includes lower surface 146 having a multiplicity of perforations 146.

In the arrangement of FIG. 5A, upper compartment 142 of balloon 140 serves to partially or fully occlude the vessel, while lower compartment 144 delivers blood to the distal vessel. Optionally, separate balloons could be used instead of dual layer balloon 140, although the dual layer construction of balloon 140, more preferably disk-shaped, may be desirable to shorten the balloon so it may be readily inserted into a highly atherosclerotic vessel. In addition, the multiplicity of perforations 148 will ensure that blood is reperfused into the vessel away from the vessel wall. FIG. 5B depicts an alternative embodiment of a dual-layer balloon having sealed and perforated compartments similar to the design of FIG. 5A. Dual-layer balloon 150 differs from balloon 140 principally in that the top surface of balloon 150 forms funnel shape 152, while perforated lower surface 154 of the balloon also may be inclined relative to the vessel wall, to further distribute blood reperfused into the vessel. In such embodiments of FIGS. 5A and 5B, it may be desirable to place the vessel pressure sensor within the vessel downstream of perforated lower surface 154.

Figure 6:
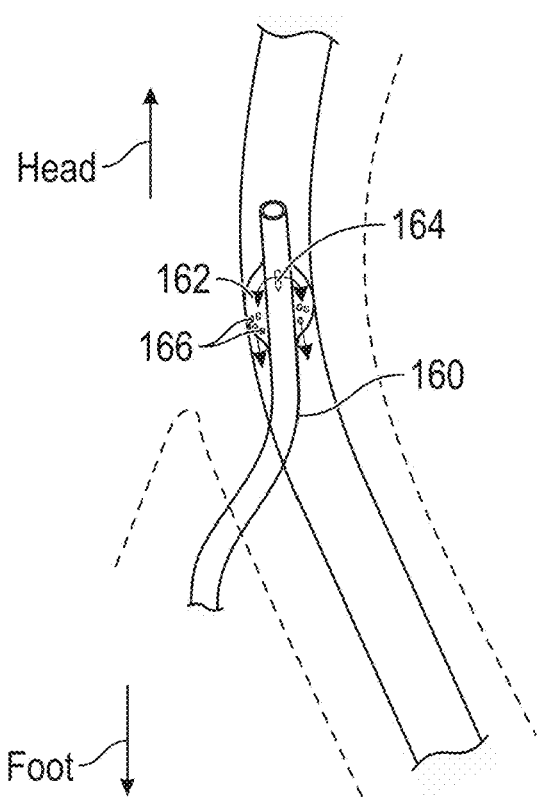
FIG. 6 is another alternative embodiment of the perfusion cannula of FIG. 4, in which the occlusion balloon is expanded with blood delivered by the extracorporeal pump to occlude, partially or fully, antegrade flow while a perforated proximal face of the balloon disperses blood delivered by the extracorporeal pump to provide an antegrade flow with controlled volume and pressure.

Referring now to FIG. 6, a further alternative embodiment of a perfusion system of the present invention is described. In FIG. 6, elements of the system that are common to the embodiments of FIG. 2A and FIG. 3A are omitted for clarity. Cannula 160 is a dual lumen cannula as described above with respect to FIG. 2A. Balloon 162 is affixed to the cannula so that the interior of balloon 162 communicates with skive 164, through which blood is delivered by the extracorporeal pump (e.g., pump 76 of FIG. 2A) into the vessel. Balloon 162 includes a multiplicity of perforations 166 in its lower surface. In this manner, balloon 162 expands at least partially to occlude the vessel when blood from the extracorporeal pump is delivered into the interior of balloon 162. The blood then exits balloon 162 through a multiplicity of perforations 166 and flows in an antegrade fashion to the patient's extremities. In such embodiments of FIG. 6, it may be desirable to place the vessel pressure sensor within the vessel downstream of balloon 162.

Figure 7:
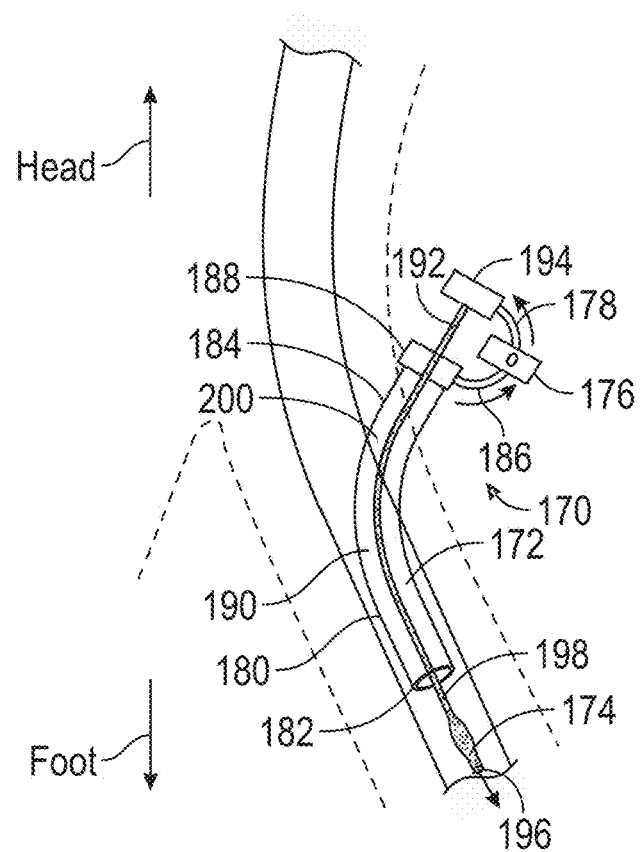
FIG. 7 is a schematic view of a perfusion system of the present invention wherein coaxial inlet and return catheters are coupled to an extracorporeal pump.

FIG. 7 depicts a further alternative embodiment of a perfusion system constructed in accordance with the principles of the present invention. System 170 differs from the preceding embodiments in that its inlet catheter may be employed to perform an interventional procedure, e.g., to treat peripheral artery disease, and thereafter used as part of a perfusion system to reduce the risk of limb ischemia. As depicted in FIG. 7, system 170 includes inlet cannula 172 and return catheter 174 coupled to extracorporeal pump 176 by tubing 178. Extracorporeal pump 176 may be any of the pumps described throughout this specification.

Inlet cannula 172 has distal end 180 having inlet 182, proximal end 184 including outlet port 186 and hemostatic port 188, and inlet lumen 190 extending between distal end 180 and proximal end 184 and also in fluid communication with outlet port 186. Inlet cannula 172 is configured to be placed in an antegrade manner in a limb, such as an arm or leg, for performing an interventional procedure. Once that treatment is completed, inlet cannula 172 may be left in place and employed as part of the perfusion system, as described below.

Return cannula 174 has proximal end 192 including inlet port 194, outlet 196 and lumen 198 extending therebetween. Return cannula 174 preferably is longer than inlet cannula 172, and has a diameter selected so that, when inserted through inlet cannula 172, annulus 200 is created in inlet lumen 190 to permit blood to be drawn through inlet 182, annulus 200 and outlet port 186 to extracorporeal pump 176. Return catheter 174 is inserted through hemostatic port 188. The inlet and outlet cannulas then may be coupled to extracorporeal pump 176 by tubing 178. In operation, pump 176 draws blood through inlet 182, annulus 200 and outlet port 186 to the pump and then expels the blood through inlet port 194, lumen 198 and outlet 196 of return cannula 174 in an antegrade direction into the vessel, at a controlled pressure or flow rate determined by pump 176 based on user input, or as determined by the pump controller. Alternatively, return cannula 174 could be placed in the patient's contralateral arm or leg, as may be required to reduce the risk of limb ischemia.

In a yet further embodiment, an inlet cannula may be inserted in more than one artery or vein, and blood delivered by the extracorporeal pump may be reperfused to more than one extremity. For example, an extracorporeal pump may include two or more inlets, such that one inlet may be connected to a cannula located in an artery and a second inlet may be coupled to a cannula placed in a vein of a limb. Blood delivered by the extracorporeal pump may be reperfused into the artery downstream of an obstruction, while venous blood may be drawn from the limb, thereby creating a further gradient to enhance perfusion of the limb. Alternatively, an extracorporeal system of the invention may be configured to have a single inlet but multiple outlets, so that oxygenated blood directed to the pump may be reperfused in multiple limbs. In another alternative embodiment, the return cannula may deliver the blood to afferent lymph vessels of the lymphatic system to reduce or prevent venous thrombosis, peripheral edema or lymphedema.

Figure 8:
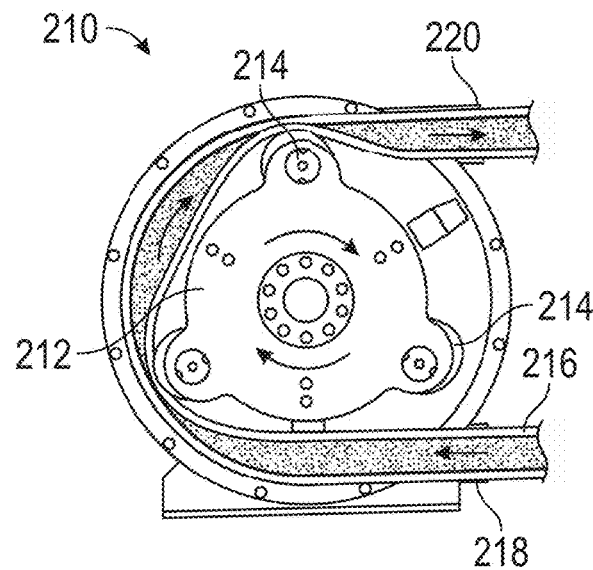
FIG. 8 is an exemplary roller-type pump for providing pulsatile flow, suitable for use in the perfusion system of the present invention.

Referring now to FIG. 8, exemplary mechanism 210 for a roller-type pump suitable for use as the extracorporeal pump of the perfusion system. As will be understood by persons of skill in the art of pump design, mechanism 210 includes rotor 212 that carries three or more rollers 214. Rollers 214 contact plastic tubing 216, which tubing connected to inlet port 218 and outlet port 220 of the pump. Rotor 212 is mounted on axle 222 that is coupled to an electric motor (not shown) either directly or via a suitable gear train, so that rotation of the rotor causes rollers 214 to ride along plastic tubing 216 to propel blood within the tubing from the inlet port 218 to outlet port 220. U.S. Pat. No. 3,963,023 to Hankinson, incorporated herein by reference, provides additional details for roller pumps of the type depicted in FIG. 8. A suitable alternative blood pump design capable of generating pulsatile flow is described in U.S. Pat. No. 9,295,767 to Schmid, also incorporated herein by reference. U.S. Pat. No. 4,468,177 to Strimling describes a diaphragm type pump suitable for use as the extracorporeal pump of the inventive perfusion system, and is also incorporated here by reference.

Figure 9A:
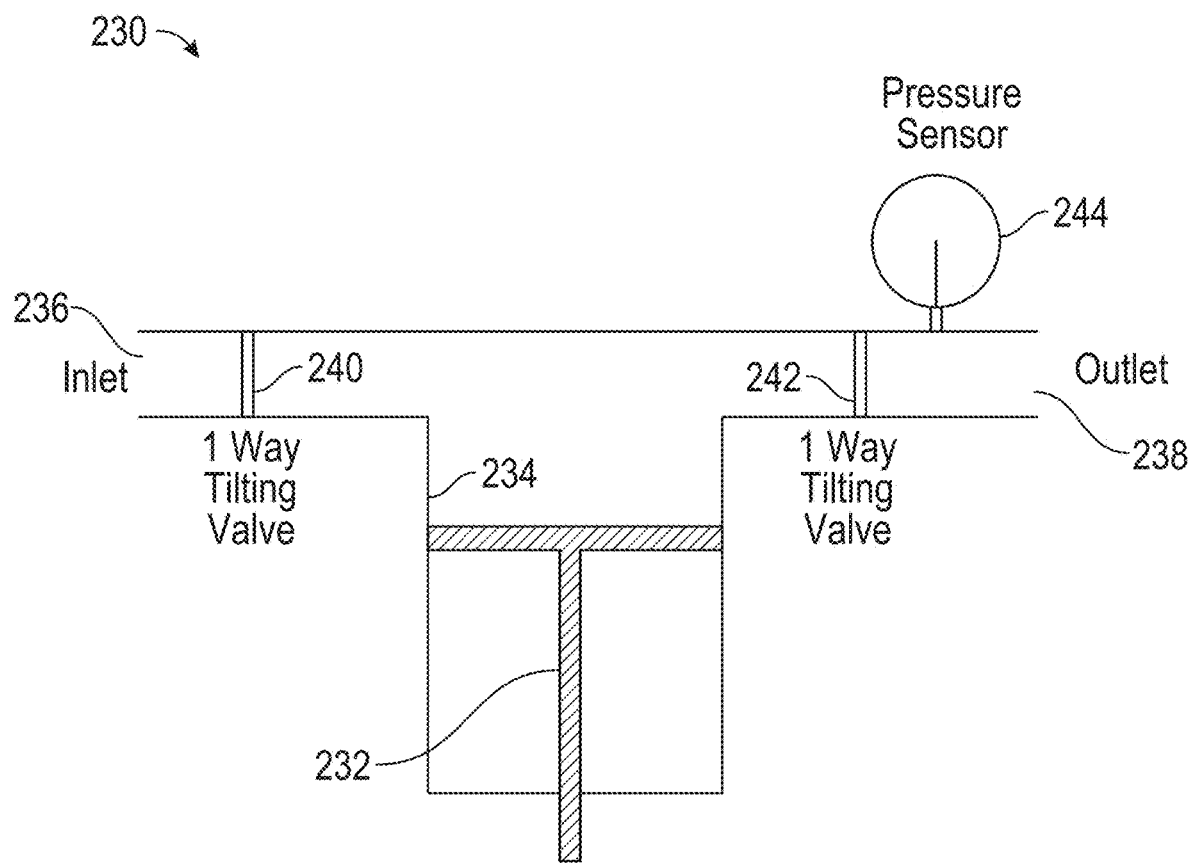
FIGS. 9A, 9B and 9C are schematic views of the operation of a piston-style pump for generating pulsatile flow, suitable for use in the perfusion system of the present invention.
Figure 9B:
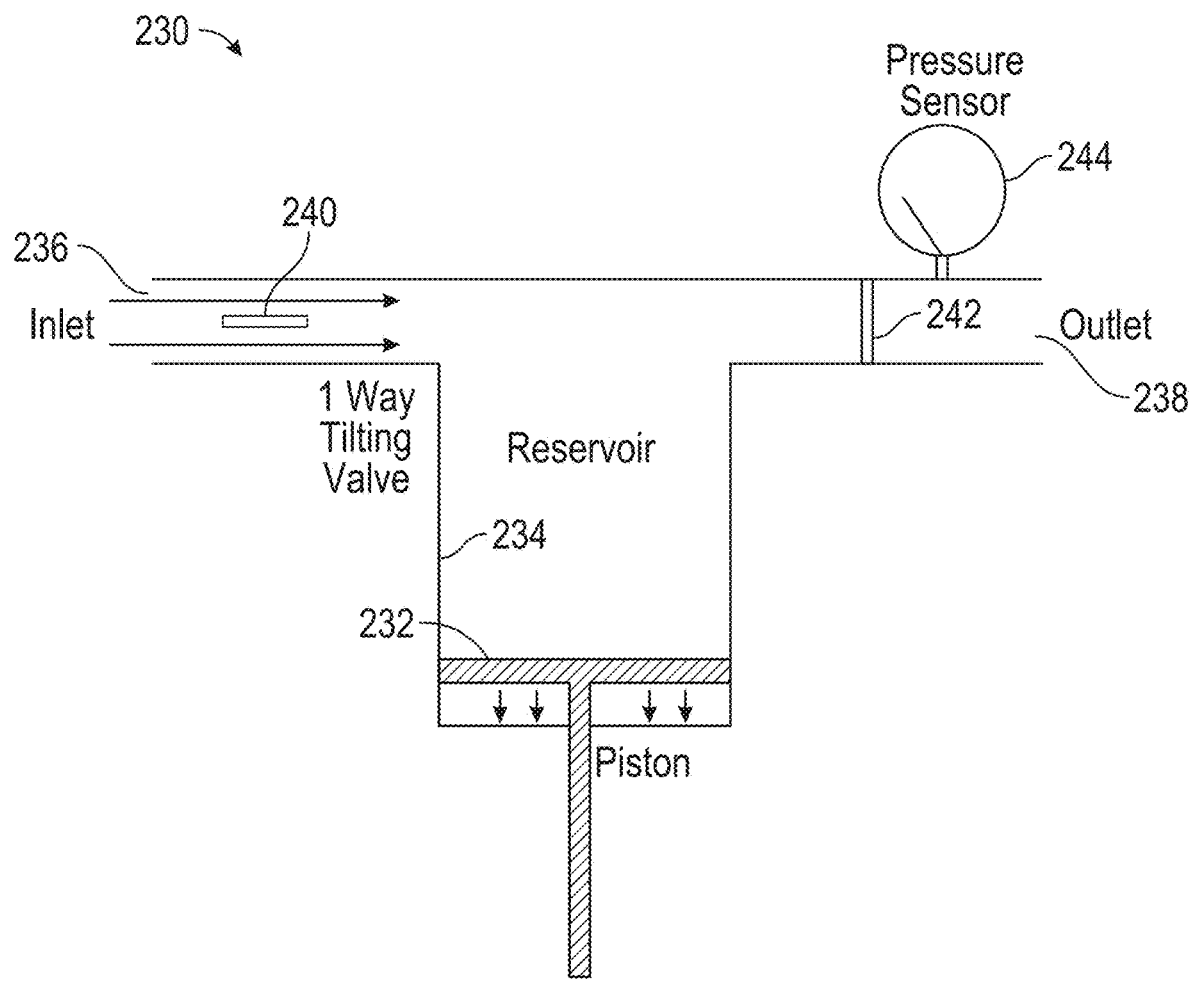
Figure 9C:
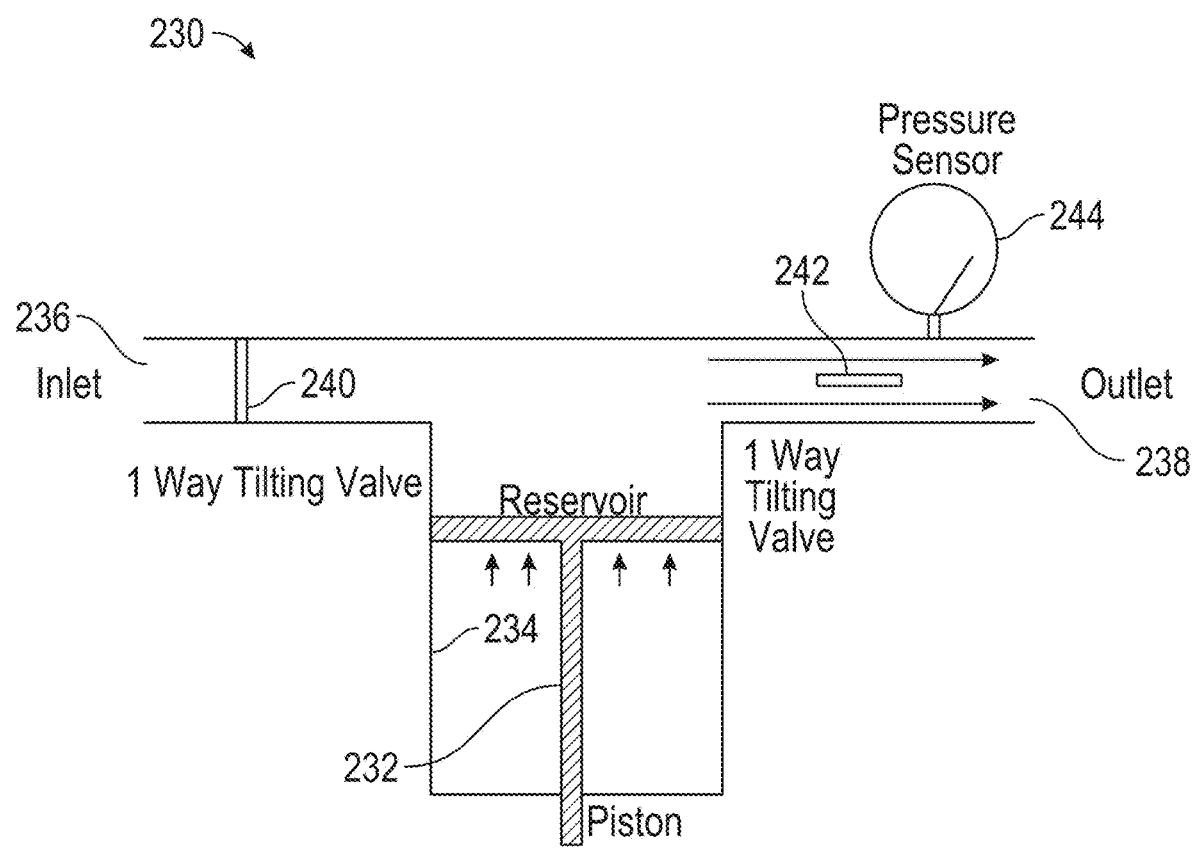

Referring now to FIGS. 9A, 9B and 9C, a piston-type mechanism for use as the extracorporeal pump of the inventive system is described. Pump 230 includes piston 232 arranged to reciprocate within chamber 234, which communicates with inlet 236 and outlet 238. As will be understood by one of skill in the art of pump design, piston 232 is coupled to an electric motor via a gear system (not shown) that cyclically advances and retracts the piston head within chamber 234. One-way valve 240, e.g., a butterfly valve or flap valve, is located distal of inlet 236 and another one-way valve 242 is located proximal of outlet 238. Pressure sensor 244 monitors pressure within the conduit distal to outlet 238. In FIG. 9A, pump 230 is shown in an equipoise condition, in which blood is not being drawn into or expelled from chamber 234. In the event pressure sensor 244 detects a high pressure within the conduit while the vessel pressure sensor detects a low pressure, it may indicate that the tubing is blocked, clotted or kinked. The controller may signal an alarm based on detection of a pressure differential exceeding a predetermined threshold.

FIG. 9B depicts an intake stroke of pump 230, during which inlet valve 240 opens to permit blood to be drawn into chamber 234 during retraction of piston 232. During this phase of operation, one-way valve 242 is closed and pressure sensor 244 registers a negative pressure. Once the piston reaches its minimum stroke, it reverses direction, causing one-way valve 240 to close and one-way valve 242 to open, and thus permit blood to flow through outlet 238. During this phase of operation, pressure sensor 244 registers a positive pressure. When piston 232 reaches its maximum stroke, it begins to reverse direction, thereby causing one-way valve 242 to close and one-way valve 240 again to open. In this manner, depending upon the speed at which the electric motor and gear train drives piston 232, a specified blood flow rate or pressure may be obtained at outlet 238. U.S. Pat. No. 4,221,548 to Child describes an alternative embodiment of a piston pump, incorporated by reference here, suitable for use in the perfusion system of the present invention.

Figure 10A:
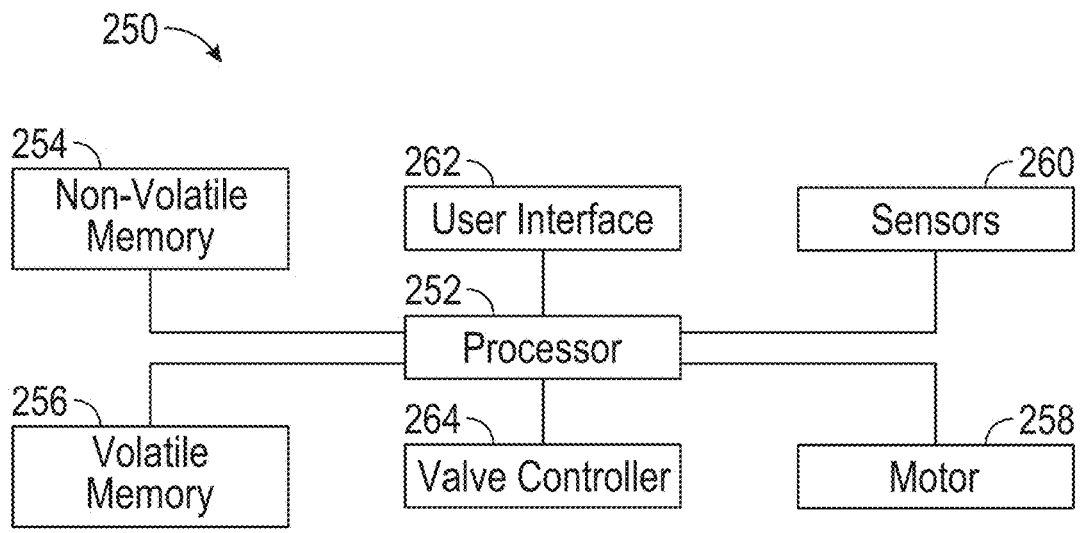
FIGS. 10A and 10B are, respectively, a schematic block diagram of extracorporeal pump and software for use in an exemplary controller for controlling operation of an extracorporeal pump employed in the perfusion system of the present invention.
Figure 10B:
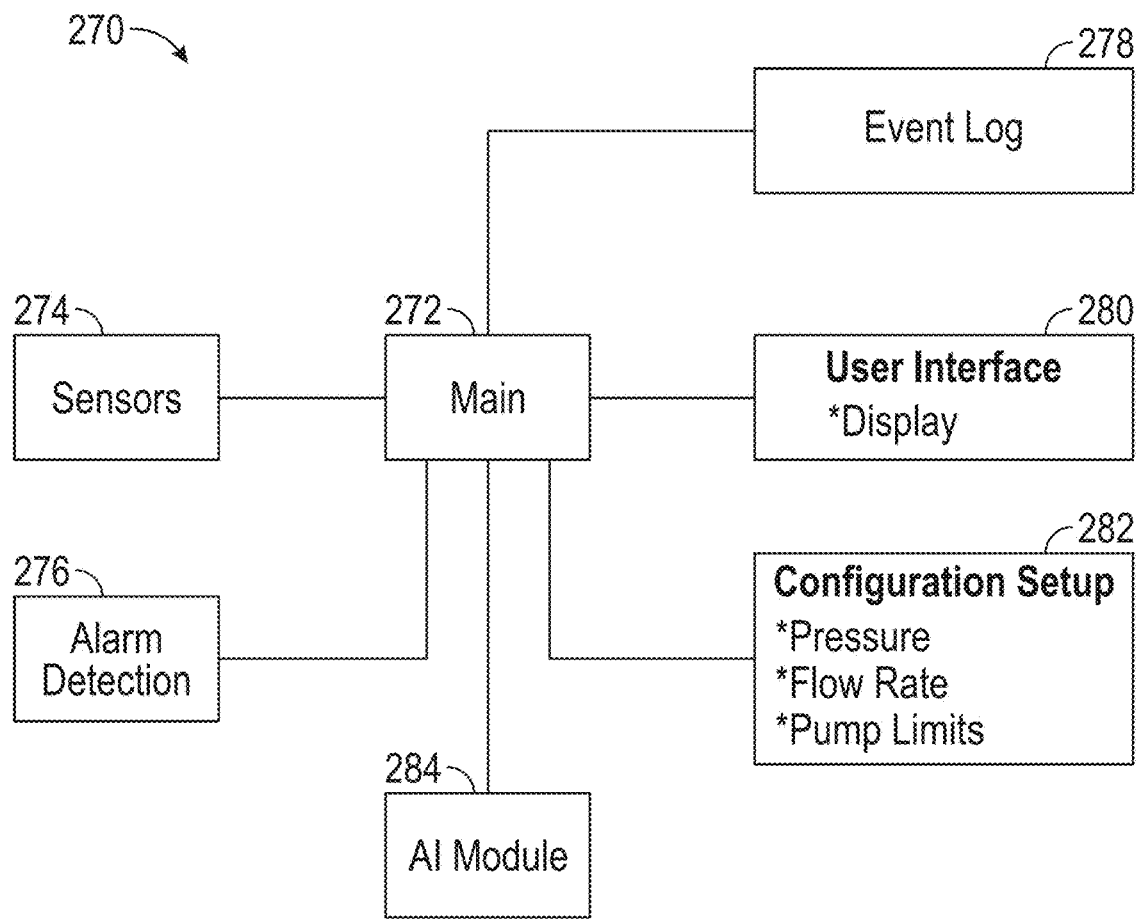

FIGS. 10A and 10B are, respectively, an exemplary schematic of an extracorporeal pump and software for operating the system. More particularly, FIG. 10A is a schematic depicting the functional blocks of extracorporeal pump 250 for use in a perfusion system of the present invention and includes processor 252 coupled to nonvolatile memory 254, such as flash memory, electrically erasable programmable read only memory and/or a hard disk, and volatile memory 256 via data buses. Processor 252 is electrically coupled to electric motor 258, a plurality of sensors 260, user interface 262 and valve controller 264.

Motor 258 may include a separate dedicated controller, which interprets and actuates motor 258 responsive to commands from processor 252.

Processor 252 executes programming, described with respect to FIG. 10B, stored in nonvolatile memory 254 that controls operation of motor 258 responsive to signals generated by sensors 260 and input from user interface 262. Processor 252 is configured to monitor operation of motor 258 (and any associated motor controller) and sensors 260, as described below, and to store data reflecting operation of the pump, including event logs and alarms.

Nonvolatile memory 254 preferably comprises flash memory, EEPROM or a solid state or hard disk, and stores a unique device identifier for the pump, and firmware and programming to be executed by processor 252, configuration set point data relating to operation of the pump. Volatile memory 256 is coupled to and supports operation of processor 252, and stores data and event log information gathered during operation of pump 250.

Motor 258 is of a type selected to drive the pumping mechanism of the extracorporeal pump such as described above. User interface 262 may include an input device, e.g., corresponding to display panels 17 and 77 described above, or include input keys and a display for displaying input pump operational parameters, pump status and sensed data. Sensors 260 may include pressure sensors at the inlet port and outlet port of the pump, pressure sensors in the artery or vein upstream of the inlet of the inlet cannula(s) and downstream of the outlet of the return cannula(s), blood and/or tissue oxygenation sensors such as NIRS, pH and/or lactate level sensors, as well as a flow sensor to determine the rate of flow of blood through the pump. Sensors 260 may be monitored by processor 252 to determine inlet and outlet blood pressures, tissue oxygenation, and the occurrence of obstructions within the blood circuit.

Processor 252 may be in communication with valve controller 264; alternatively, valve controller 264 may be part of the functionality of processor 252. Valve controller 264 controls the actuation of any valves that may be used to control the flow of blood from the inlet port to the outlet port. Valve controller 264 also may coordinate the actuation of one-way valves in the embodiment of FIGS. 9A to 9C.

Turning now to FIG. 10B, software 270 for operating extracorporeal pump 250 of FIG. 10A is described. It will be understood that software 270 is implemented as programming that is run by processor 252 to control, inter alia, operation of motor 258 of the extracorporeal pump. Software 270 comprises a number of functional blocks, including main block 272, sensor block 274, alarm detection block 276, event logging block 278, user interface block 280, configuration setup block 282, and AI module 284. In one embodiment, the software is configured to run on top of a Microsoft Windows® (a registered trademark of Microsoft Corporation, Redmond, Wash.) or Unix-based operating system.

Main block 272 preferably consists of a main software routine that executes on processor 252, and controls overall operation of the other functional blocks. Main block 272 enables the operator to input operational data for the pump via User Interface 280 and User Interface 262, as well as to display operational and status data for the pump, including pump outlet pressure and/or flow rate, local blood pressure, tissue oxygenation levels, and alarm limit data. Main block 272 also controls operation of motor 258 and monitoring of sensors via Sensor block 274.

Alarm Detection block 276 may include a routine for evaluating the data received from sensors 260 to determine the occurrence of abnormal conditions for the operator's attention. For example, Alarm Detection block 276 may be configured to alert the operator to a departure of the sensor data from the preset values, or to identify potential occlusions in effecting the pump operation, or displacement of the catheter from the vessel lumen. Alarm detection block 276 also may be configured to detect an increase in vascular resistance and/or pressure in the patient's extremities, as well as potentially slow flow conditions that could lead to limb ischemia. Further, alarm detection block 276 may be configured to detect a decrease limb tissue oxygenation. Such alarms may be communicated to the operator via a display of User Interface 262. This information may be stored by Event Log block 278 in non-volatile memory 254 to create a record of the pump operational data, including pump operating times, and pressure/flow data.

User interface block 280 handles receipt of data input by the operator, as well as display of information about the pump operational status in an intuitive, easily understood format for operator review. Configuration Setup block 282 is a routine that configures the parameters stored within nonvolatile memory 254 that control operation of pump 250, including the required pump output pressure, local blood pressure, flow rate, tissue oxygenation and any limit values used to assess the occurrence of alarm conditions. Block 282 also may configure parameters stored within nonvolatile memory 254 of relating to control of operation of processor 252 and motor 258.

AI Module block 284 may include programming that permits the extracorporeal pump automatically to optimize the local blood pressure and tissue oxygenation levels for a specific patient to reduce the risk of limb ischemia. In particular, AI Module 284 may include programming that initiates pump operation at a pressure and/or tissue oxygenation level initially set by a human operator. Then, based on monitored pressure data from the limb and/or monitored tissue oxygenation levels, the AI module may step through a series of pump speeds to adjust the flow rate while also monitoring the pressure in the patient's extremities. In one embodiment, AI Module 282 then may continue further operation of the pump by selecting the pump speed that produces the highest monitored flow rate at the lowest pressure.

In an alternative embodiment, AI Module 282 may be configured to activate a built in or inline ECMO system if it is determined that increased flow rate or local blood pressure is not enough to maintain a target level of oxygenation in the tissue of the extremities. In a further embodiment, AI Module 282 may activate the ECMO to cause hyperbaric oxygenation of the blood to further increase tissue oxygenation. In yet another embodiment, the pump circuit may act as a passive bypass until sensors 260 detect tissue oxygenation levels that drop below a target value. When it is detected the tissue oxygenation levels drop below a target value, AI Module 282 then may activate the pump to increase local blood pressure in the reperfused region.

Preliminary Experimental Observations

Initial testing of the proposed reperfusion pump system and methods of the present invention has been conducted in a porcine model. The results of that testing demonstrated unexpected, beneficial results as described below.

Vascular Pressure Controlled Pump Vs Passive Bypass

Figure 11:
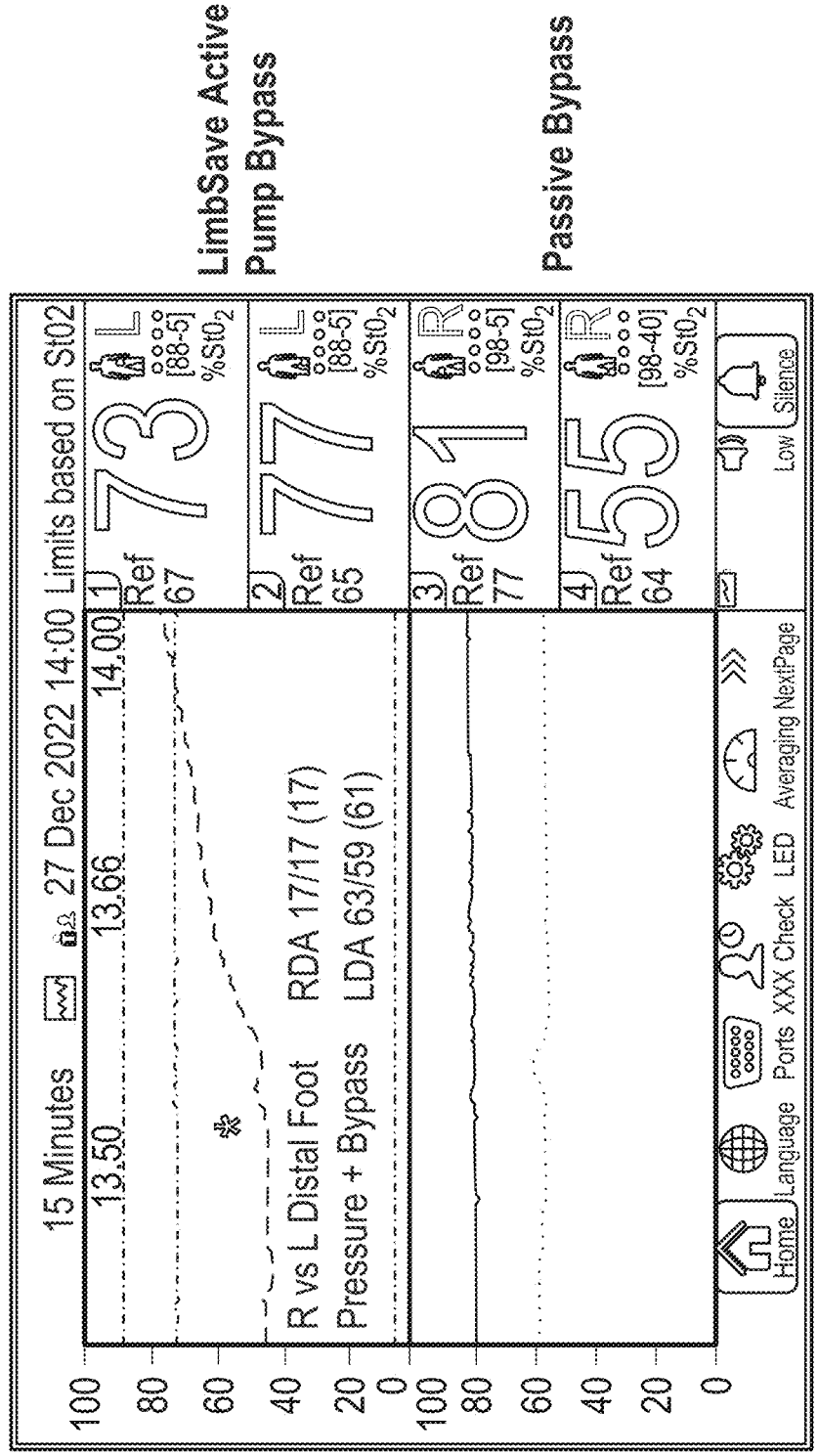
FIG. 11 is screenshot of a display showing the results of near-infrared spectroscopic monitoring of limb oxygenation in an animal test, wherein a left limb of the animal is perfused by an embodiment of the present invention and the right limb is passively perfused.

FIG. 11 is a screenshot of a display depicting vascular blood pressure and oxygen saturation in the legs of a pig. In this experiment, the inventive pump circuit was used to create a blood circuit from the carotid artery to the left leg (top graph), while a passive circuit was created by tubing inserted at one end into the other carotid artery and at the other into the right leg (bottom graph). In both legs, continuous NIRS measurements were taken to determine absolute tissue saturation (StO$_2$) levels through various stages of the reperfusion process, with the digital readouts to the right of the graphs showing the StO$_2$ levels at the end of the experiment. The top line of each graph, indicates the reference values of non-occluded regions of the animal (81% for the right leg; 73% for the left leg). The lower line in the top graph (indicated as 77% StO$_2$) corresponds to NIRS measurements of the StO$_2$ levels in the left leg (with the inventive pump circuit) after occlusion of that leg. The lower line of the lower graph (indicated as 55% StO$_2$) corresponds to NIRS measurements of the StO$_2$ levels in the right leg with just passive bypass.

At the initiation of the NIRS measurements, both legs were occluded with no form of reperfusion to reduce the StO$_2$ levels in each leg. Once quasi-static levels were reached, the NIRS measurements were recorded for five minutes before reperfusion was initiated. At the five minute mark, as noted by the asterisk (*), both the passive bypass and the inventive pump system were activated. In the left leg (top graph) it can be seen that vascular pressure controlled perfusion resulted in higher perfusion of the leg tissue as indicated by the steep curve ending at 77% StO$_2$. The right leg (bottom graph) shows that the passive bypass has little reperfusion value as indicated by the flat curve ending at 55% StO$_2$. The experiment demonstrates that a passive system does not oxygenate the tissue as much as the inventive pump circuit in which vascular blood pressure is controlled.

Absolute Tissue Saturation (StO$_2$) and the Blood's Partial Pressure of Oxygen (PaO$_2$)

Figure 12A:
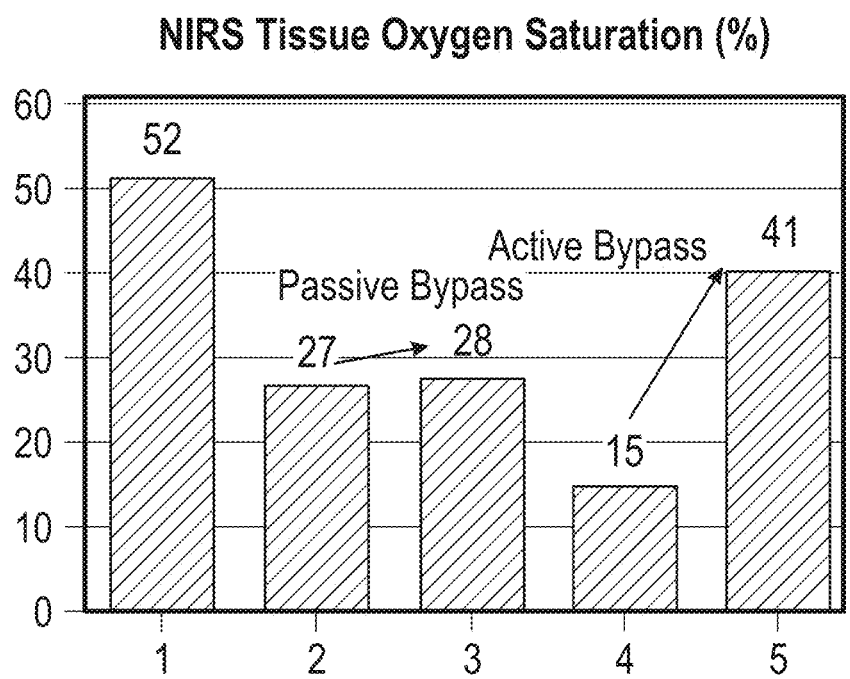
FIGS. 12A and 12B are graphs depicting tissue oxygenation and arterial blood gas values for a different animal test, demonstrating differences between active perfusion and passive perfusion.
Figure 12B:
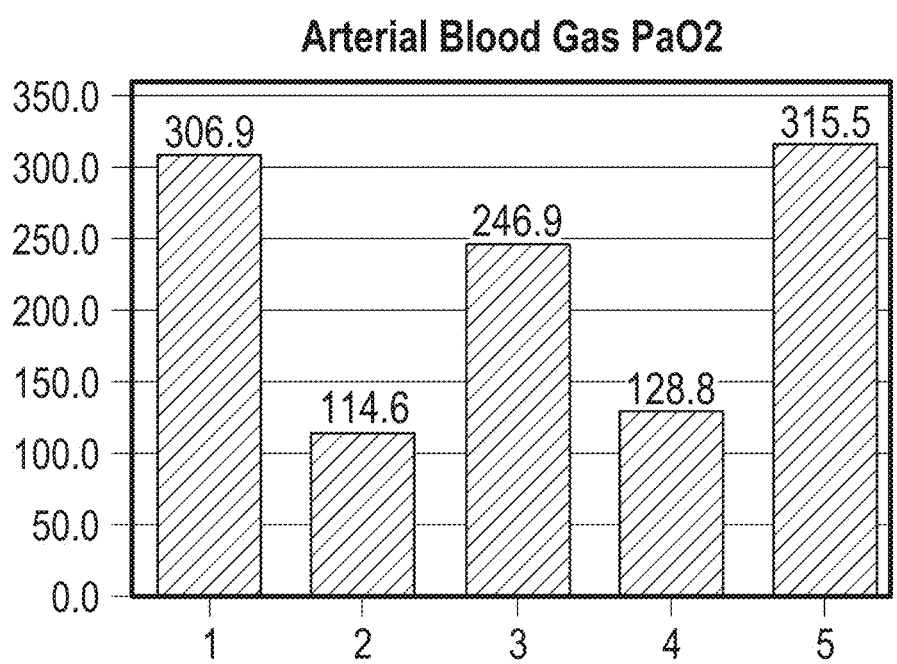

FIGS. 12A and 12B show the results of a second experiment, in which flow was occluded (the iliac artery closed off) to cause ischemia in one leg of a pig, followed by passive bypass reperfusion and then vascular controlled pressure reperfusion with the inventive pump system. FIG. 12A depicts StO$_2$ levels during five sequential intervals, while FIG. 12B depicts the PaO$_2$ levels at the same five intervals. Point 1 represents a base level of StO$_2$ and PaO$_2$ that was measured before occlusion occurred. Point 2 corresponds to occlusion of the leg for twenty minutes to induce ischemia, as shown by the drastic drop in both levels. Point 3 corresponds to provision of passive bypass for about fifteen minutes, ending at Point 4. Notably, during passive bypass, the blood oxygenation level rises substantially (to 246.9), although tissue oxygenation, as determined by the NIRS measurement, shows virtually no increase, from 27% StO$_2$ to only 28% StO$_2$. At Point 4 in FIGS. 12A and 12B, the passive bypass was terminated for about 90 seconds to return the limb to an ischemic state. Then, from points 4 to 5, the described vascular pressure-controlled system described herein was activated. After one minute, the blood oxygenation level returned to normal, from 128.8 PaO$_2$ to 315.5 PaO$_2$. Importantly, however, tissue oxygenation as measured by the NIRS sensor also rose significantly, from 15% StO$_2$ to 41% StO$_2$. The foregoing preliminary results demonstrate that reperfusing an ischemic limb at a controlled vascular pressure provides much higher oxygen uptake than simply flowing physiologic flow rates. Applicants hypothesize that vascular blood pressure causes higher oxygen exchange in the capillary beds of the limb than can be achieved merely by providing physiologic flow rates to the reperfused vessel.

While various illustrative embodiments of the invention are described above, it will be apparent to one skilled in the art that various changes and modifications may be made therein without departing from the invention.

What is claimed is:

1. A perfusion system for use with an obstruction of antegrade flow to a patient's extremity due to thrombosis, trauma, or medical procedures/devices, the perfusion system comprising:
   an inlet cannula configured to be placed in a patient's vessel, the inlet cannula having a proximal end, a distal end and a lumen extending from the proximal end to the distal end, an inlet at the distal end, an outlet port and a hemostatic port disposed on the proximal end, wherein the inlet and the hemostatic port communicate with the lumen, and the hemostatic port is configured to permit an interventional or circulatory assist device to be inserted through the lumen to form an annulus that communicates with the outlet port;
   a return lumen having a proximal end and a distal end, the distal end of the return lumen configured to be placed in the patient's vessel downstream of the obstruction;
   an extracorporeal pump configured to be coupled to the outlet port of the inlet cannula and the proximal end of the return lumen; and
   a controller operatively coupled to the extracorporeal pump, the controller configured to cause the extracorporeal pump to enter a local pressure control mode wherein the extracorporeal pump is configured to draw blood through the inlet of the inlet cannula and to deliver blood at the distal end of the return lumen to perfuse the patient's extremity at a selected local pressure, independent of operation of the interventional or circulatory assist device.

2. The perfusion system of claim 1, wherein the return lumen is disposed in a return cannula.

3. The perfusion system of claim 1, wherein the return lumen comprises a second lumen of the inlet cannula, and the distal end of the return lumen defines a skive in a lateral surface of the inlet cannula.

4. The perfusion system of claim 1, wherein the inlet catheter further comprises an occlusion balloon that at least partially occludes flow within the vessel antegrade to the inlet of the inlet cannula.

5. The perfusion system of claim 4, wherein the inlet catheter further comprises a first inflation port at the proximal end of the inlet cannula and a first inflation lumen that extends through the inlet cannula from the first inflation port to the occlusion balloon.

6. The perfusion system of claim 4, wherein inlet cannula further comprises:
   a sealing balloon disposed proximal of the occlusion balloon;
   a second inflation port at the proximal end of the inlet cannula; and
   a second inflation lumen that extends through the inlet cannula from the second inflation port to the sealing balloon.

7. The perfusion system of claim 1, wherein the extracorporeal pump further comprises an extracorporeal membrane oxygenator system.

8. The perfusion system of claim 1, wherein the extracorporeal pump is in communication with a sensor measuring at least one of tissue oxygenation, pH level, and lactate levels of the occluded limb and the controller is programmed to adjust a vessel pressure or flow rate to achieve a target tissue oxygenation level.

9. The perfusion system of claim 1, wherein the return lumen comprises a second lumen of the inlet cannula, the inlet catheter further comprises an occlusion balloon having a multiplicity of perforations, and the distal end of the return lumen communicates with an interior of the occlusion balloon.

10. The perfusion system of claim 1, wherein the controller is programmed with an AI module configured automatically to determine a preferred flow rate to achieve a target local pressure that reduces a risk of limb ischemia.

11. The perfusion system of claim 1, wherein the extracorporeal pump is in communication with a pressure sensor located in the patient's vessel antegrade to the distal end of the return lumen and the controller is programmed to monitor the pressure sensor to determine occurrence of an occlusion.

12. The perfusion system of claim 1, wherein the controller is configured to cause the extracorporeal pump to transition between the local pressure control mode and a flow mode, and wherein, in the flow mode, the controller is configured to cause the extracorporeal pump to pump at a set flow rate to perfuse the patient's extremity.

13. A perfusion system comprising:
at least one inlet cannula configured to be placed in a patient's vasculature, the at least one inlet cannula having a proximal end, a distal end and a lumen extending from the proximal end to the distal end, an inlet at the distal end, an outlet port disposed on the proximal end, wherein the inlet communicates with the lumen;
at least one return lumen having a proximal end and a distal end, the distal end of the at least one return lumen configured to be placed in the patient's vasculature at one or more locations downstream of the inlet of the at least one inlet cannula; and
an extracorporeal pump configured to be coupled to the outlet port of the at least one inlet cannula and the proximal end of the at least one return lumen; and
a controller operatively coupled to the extracorporeal pump, the controller configured to cause the extracorporeal pump to enter a local pressure control mode wherein the extracorporeal pump is configured to draw blood through the inlet of the at least one inlet cannula and to deliver blood through the distal end of the at least one return lumen to perfuse the patient's extremity at a selected local pressure.

14. The perfusion system of claim 13, wherein the at least one return lumen is disposed in at least one return cannula, and wherein the at least one inlet cannula further comprises a hemostatic port disposed on the proximal end, the hemostatic port is configured to permit an interventional or circulatory assist device to be inserted through the lumen to form an annulus that communicates with the outlet port.

15. The perfusion system of claim 14, wherein the at least one return cannula is configured to be inserted through the hemostatic port of the at least one inlet cannula to form an annulus that communicates with the outlet port of the at least one inlet cannula.

16. The perfusion system of claim 13, wherein the extracorporeal pump is selected from amongst a vane pump, a centrifugal pump, a roller pump, an axial flow pump, a diaphragm pump and a piston pump, and wherein the extracorporeal pump is configured to generate pulsatile flow at the distal end of the return lumen.

17. The perfusion system of claim 13, wherein the return lumen further comprises at least one delivery port configured to deliver one or more reperfusion protection agents or donor blood for a transfusion.

18. The perfusion system of claim 13, wherein the extracorporeal pump comprises an electric motor, and wherein the controller is programmed to control operation of the electric motor.

19. The perfusion system of claim 13, wherein the controller is programmed to maintain the selected local pressure at the distal end of the at least one return lumen via regulating a flowrate, and wherein the selected local pressure is input via a user interface.

20. The perfusion system of claim 13, wherein the controller is programmed with an AI module configured automatically to determine a preferred flow rate in order to achieve a target local pressure that reduces a risk of limb ischemia.

21. The perfusion system of claim 13, wherein the extracorporeal pump is in communication with a pressure sensor located in the patient's vasculature downstream of the distal end of the at least one return lumen and the controller is programmed to monitor the pressure sensor to determine occurrence of an occlusion, and wherein the controller is programmed to generate an alarm if a monitored pressure sensor deviates from a preselected limit value.

22. The perfusion system of claim 13, wherein the extracorporeal pump comprises a first extracorporeal pump and a second extracorporeal pump, wherein the at least one inlet cannula comprises a first inlet cannula having a first inlet configured to be placed within a patient's vein and a second inlet cannula having a second inlet configured to be placed within a patient's artery, wherein the first extracorporeal pump is configured to draw blood through the first inlet and return the blood via the outlet to a vein distal to an occlusion, and wherein the second extracorporeal pump is configured to draw blood through the second inlet and deliver the blood via the outlet to an artery distal to an occlusion.

23. The perfusion system of claim 13, wherein the extracorporeal pump comprises a first motor and a second motor, wherein the at least one inlet cannula comprises a first inlet cannula having a first inlet configured to be placed within a patient's vein and a second inlet cannula having a second inlet configured to be placed within a patient's artery, wherein the first motor is configured to draw blood through the first inlet and return the blood via the outlet to a vein distal to an occlusion, and wherein the second motor is configured to draw blood through the second inlet and return the blood via the outlet to an artery distal to an occlusion.

24. A perfusion system for returning blood accumulated within a patient's cavity to systemic circulation, the perfusion system comprising:
an inlet cannula configured to be placed in a patient's cavity, the inlet cannula having a proximal end, a distal end and a lumen extending from the proximal end to the distal end, an inlet at the distal end, an outlet port disposed on the proximal end, and wherein the inlet communicates with the lumen;
a return lumen having a proximal end and a distal end, the distal end of the return lumen configured to be placed in a patient's vessel;
an extracorporeal pump configured to be coupled to the outlet port of the inlet cannula and the proximal end of the return lumen; and
a controller operatively coupled to the extracorporeal pump, the controller configured to cause the extracorporeal pump to enter a local pressure control mode wherein the extracorporeal pump is configured to draw blood through the inlet of the inlet cannula and to deliver blood at the distal end of the return lumen to perfuse the patient's extremity at a selected local pressure.

25. The perfusion system of claim 24, wherein the inlet cannula further comprises a hemostatic port in communication with the lumen, wherein the hemostatic port is configured to permit an interventional or circulatory assist device to be inserted through the lumen to form an annulus that communicates with the outlet port.

26. The perfusion system of claim 24, wherein the patient's cavity is a pericardium.

27. The perfusion system of claim 24, wherein the distal end comprises a pigtail catheter.

28. The perfusion system of claim 24, wherein the return lumen further comprises at least one delivery port configured to deliver one or more reperfusion protection agents or donor blood for a transfusion.

\* \* \* \* \*